US012569650B2

(12) United States Patent
Herrera

(10) Patent No.: US 12,569,650 B2
(45) Date of Patent: Mar. 10, 2026

(54) URINARY CATHETER WITH RETENTION FEATURES

(71) Applicant: Spinal Singularity, Inc., San Clemente, CA (US)

(72) Inventor: Derek Herrera, San Clemente, CA (US)

(73) Assignee: UROFLOW TECHNOLOGY, LLC, Irvine, CA (US)

( * ) Notice: Subject to any disclaimer, the term of this patent is extended or adjusted under 35 U.S.C. 154(b) by 642 days.

(21) Appl. No.: 17/866,490

(22) Filed: Jul. 16, 2022

(65) Prior Publication Data

US 2023/0001155 A1 Jan. 5, 2023

Related U.S. Application Data

(63) Continuation-in-part of application No. 16/436,773, filed on Jun. 10, 2019, now Pat. No. 11,628,271.

(51) Int. Cl.
*A61M 25/02* (2006.01)
*A61M 25/00* (2006.01)

(52) U.S. Cl.
CPC ........ *A61M 25/02* (2013.01); *A61M 25/0017* (2013.01); *A61M 25/0023* (2013.01); *A61M 2025/0206* (2013.01)

(58) Field of Classification Search
CPC .............. A61M 25/02; A61M 25/0017; A61M 25/0023; A61M 2025/0206; A61M 25/04; A61M 2025/1004; A61M 27/002; A61M 25/10; A61M 25/1002; A61M 2210/1085;

A61M 25/002; A61M 25/0111; A61M 2025/1084; A61M 25/1038; A61M 25/0082; A61M 2210/1089;
(Continued)

(56) References Cited

U.S. PATENT DOCUMENTS

| | | | |
|---|---|---|---|
| 3,630,206 A | 12/1971 | Gingold | |
| 3,713,447 A | 1/1973 | Adair | |

(Continued)

FOREIGN PATENT DOCUMENTS

| | | |
|---|---|---|
| EP | 1096900 | 9/2005 |
| EP | 1096900 B1 | 9/2005 |

(Continued)

*Primary Examiner* — Nicholas J. Weiss
*Assistant Examiner* — Brandon W. Levy
(74) *Attorney, Agent, or Firm* — SNELL & WILMER L.L.P.

(57) ABSTRACT

A urinary catheter can be retained inside the body for extended periods. A catheter mating device can connect to the catheter to move the catheter inside of the body or remove it from the body. The catheter includes: (1) a tube having a lumen and an outer surface, (2) a retainer that may have an attachment portion attached to the tube and a flap or handle-shaped structure attached to the attachment portion, wherein the retainer has a first, contracted position and a second, extended position, and (3) an bladder retention structure at the catheter's distal end, wherein the bladder retention portion may comprise a flap or a handle-shaped portion and that has a first, compressed position and a second, extended position. The retainer and/or bladder retention structure each are configured to retain the catheter in the proper position inside of a user's body.

19 Claims, 23 Drawing Sheets

(58) Field of Classification Search
CPC ....... A61M 2202/0496; A61B 5/02042; A61B
5/208; A61B 5/686; A61B 5/14539; A61B
5/204; A61B 5/6852; A61B 5/1116; A61B
2505/03; A61B 5/01; A61B 5/14507;
A61B 5/14546; A61B 5/205; A61B
5/6874; A61B 5/6882; A61B 5/002; A61B
2017/3486; A61B 17/3421; A61F 5/451;
A61F 2/0027
See application file for complete search history.

(56) References Cited

U.S. PATENT DOCUMENTS

| | | | |
|---|---|---|---|
| 3,812,841 A | 5/1974 | Isaacson | |
| 3,938,529 A | 2/1976 | Gibbons | |
| 4,043,346 A | 8/1977 | Mobley | |
| 4,168,699 A | 9/1979 | Hauser | |
| 4,710,169 A | 12/1987 | Christopher | |
| 4,932,938 A * | 6/1990 | Goldberg | A61F 2/0022 |
| | | | 604/99.04 |
| 4,986,810 A | 1/1991 | Semrad | |
| 5,041,092 A | 8/1991 | Barwick | |
| 5,140,999 A | 8/1992 | Ardito | |
| 5,366,506 A | 11/1994 | Davis | |
| 5,380,268 A | 1/1995 | Wheeler | |
| 5,411,507 A | 5/1995 | Heckele | |
| 5,476,434 A | 12/1995 | Kalb et al. | |
| 5,628,770 A | 5/1997 | Thome et al. | |
| 5,713,877 A | 2/1998 | Davis | |
| 5,749,826 A | 5/1998 | Faulkner | |
| 6,053,897 A | 4/2000 | Sachse | |
| 6,066,088 A | 5/2000 | Davis | |
| 6,132,365 A | 10/2000 | Sigurdsson | |
| 6,167,886 B1 | 1/2001 | Engel | |
| 6,527,702 B2 | 3/2003 | Whalen | |
| 6,565,536 B1 | 5/2003 | Sohn | |
| 6,602,243 B2 | 8/2003 | Noda | |
| 6,638,208 B1 | 10/2003 | Natarajan et al. | |
| 6,835,183 B2 | 12/2004 | Lennox et al. | |
| 7,001,327 B2 | 2/2006 | Whalen | |
| 7,147,606 B1 | 12/2006 | Chang et al. | |
| 7,338,028 B2 | 3/2008 | Zimmerling et al. | |
| 7,415,308 B2 | 8/2008 | Gerber et al. | |
| 7,803,106 B2 | 9/2010 | Whalen et al. | |
| 8,801,697 B2 | 8/2014 | Yugari | |
| 8,882,652 B2 | 11/2014 | Vitzthum | |
| 9,011,314 B2 | 4/2015 | Davis et al. | |
| 9,452,278 B2 | 9/2016 | Davis et al. | |
| 9,775,698 B2 | 10/2017 | Herrera et al. | |
| 10,675,134 B2 | 6/2020 | Herrera | |
| 10,675,435 B2 | 6/2020 | Herrera | |
| 10,743,975 B2 | 8/2020 | Herrera | |
| 10,751,506 B2 | 8/2020 | Herrera | |
| 2002/0010476 A1 | 1/2002 | Mulholland | |
| 2002/0107540 A1 | 8/2002 | Whalen | |
| 2002/0143293 A1 | 10/2002 | Finchbaugh | |
| 2002/0165427 A1 | 11/2002 | Yachia et al. | |
| 2002/0198506 A1 | 12/2002 | Whalen | |
| 2003/0153873 A1 | 8/2003 | Luther et al. | |
| 2003/0167069 A1 | 9/2003 | Gonzales | |
| 2003/0208183 A1 | 11/2003 | Whalen | |
| 2003/0229263 A1 | 12/2003 | Connors et al. | |
| 2004/0019369 A1 | 1/2004 | Duncan et al. | |
| 2004/0068252 A1 | 4/2004 | Whitmore et al. | |
| 2004/0106899 A1 | 6/2004 | McMichael et al. | |
| 2004/0158231 A1 * | 8/2004 | Tanghoj | A61M 25/0067 |
| | | | 604/544 |
| 2005/0049575 A1 * | 3/2005 | Snell | A61M 25/0017 |
| | | | 604/544 |

| | | | |
|---|---|---|---|
| 2005/0054995 A1 | 3/2005 | Barzell et al. | |
| 2005/0177102 A1 | 8/2005 | Hart | |
| 2005/0216069 A1 | 9/2005 | Cohen et al. | |
| 2006/0020297 A1 | 1/2006 | Gerber | |
| 2006/0184090 A1 | 8/2006 | Davis et al. | |
| 2006/0211946 A1 | 9/2006 | Mauge et al. | |
| 2006/0247723 A1 | 11/2006 | Gerber et al. | |
| 2008/0269546 A1 | 10/2008 | Wilkie et al. | |
| 2008/0294069 A1 | 11/2008 | Stickler et al. | |
| 2009/0157053 A1 | 6/2009 | Davis et al. | |
| 2010/0234876 A1 | 9/2010 | Watson | |
| 2010/0312225 A1 | 12/2010 | Armistead | |
| 2010/0331825 A1 | 12/2010 | Hakky | |
| 2011/0054404 A1 | 3/2011 | Tanabe et al. | |
| 2011/0066139 A1 | 3/2011 | Winegar | |
| 2012/0053485 A1 * | 3/2012 | Bloom | A61M 25/1002 |
| | | | 600/104 |
| 2012/0316584 A1 | 12/2012 | Miles | |
| 2013/0041430 A1 | 2/2013 | Wang et al. | |
| 2013/0090630 A1 | 4/2013 | Winegar | |
| 2013/0231639 A1 | 9/2013 | Tatlow | |
| 2014/0148648 A1 | 5/2014 | Tycast et al. | |
| 2014/0213979 A1 | 7/2014 | Boyco et al. | |
| 2014/0214009 A1 | 7/2014 | Reyes | |
| 2014/0371803 A1 | 12/2014 | Grill et al. | |
| 2015/0087896 A1 | 3/2015 | Wei et al. | |
| 2015/0250991 A1 | 9/2015 | Silvestro | |
| 2015/0366462 A1 | 12/2015 | Ramos et al. | |
| 2016/0000641 A1 | 1/2016 | Driscoll et al. | |
| 2016/0279389 A1 | 9/2016 | Rosenberg | |
| 2016/0287847 A1 | 10/2016 | Herrera | |
| 2016/0354193 A1 | 12/2016 | McNab | |
| 2017/0079761 A1 | 3/2017 | Connors | |
| 2017/0156838 A1 | 6/2017 | Herrera | |
| 2018/0036107 A1 | 2/2018 | Herrera | |
| 2018/0140799 A1 * | 5/2018 | Herrera | A61B 5/205 |
| 2018/0153669 A1 | 6/2018 | Herrera | |
| 2018/0153670 A1 | 6/2018 | Herrera | |
| 2018/0153671 A1 | 6/2018 | Herrera | |
| 2018/0264226 A1 | 9/2018 | Erbey | |
| 2020/0375714 A1 | 12/2020 | Herrera | |
| 2020/0384241 A1 | 12/2020 | Herrera | |
| 2020/0406004 A1 | 12/2020 | Herrera | |
| 2021/0121097 A1 | 4/2021 | Herrera | |
| 2021/0267740 A1 | 9/2021 | Herrera | |
| 2023/0001155 A1 | 1/2023 | Herrera | |

FOREIGN PATENT DOCUMENTS

| | | |
|---|---|---|
| EP | 2094343 | 10/2017 |
| EP | 2094343 B1 | 10/2017 |
| EP | 3247309 | 11/2017 |
| EP | 3247309 B1 | 11/2017 |
| WO | 2000002499 A1 | 1/2000 |
| WO | WO2000002499 | 1/2000 |
| WO | 2001010358 A1 | 2/2001 |
| WO | WO2001010358 | 2/2001 |
| WO | 2011032150 A1 | 3/2011 |
| WO | WO2011032150 | 3/2011 |
| WO | 2016118943 A2 | 7/2016 |
| WO | WO2016118943 | 7/2016 |
| WO | 2017015351 A2 | 1/2017 |
| WO | WO2017015351 | 1/2017 |
| WO | 2017172998 A1 | 10/2017 |
| WO | WO2017172998 | 10/2017 |
| WO | 2018200643 A1 | 11/2018 |
| WO | WO2018200643 | 11/2018 |
| WO | 2019068104 A1 | 4/2019 |
| WO | WO2019068104 | 4/2019 |

* cited by examiner

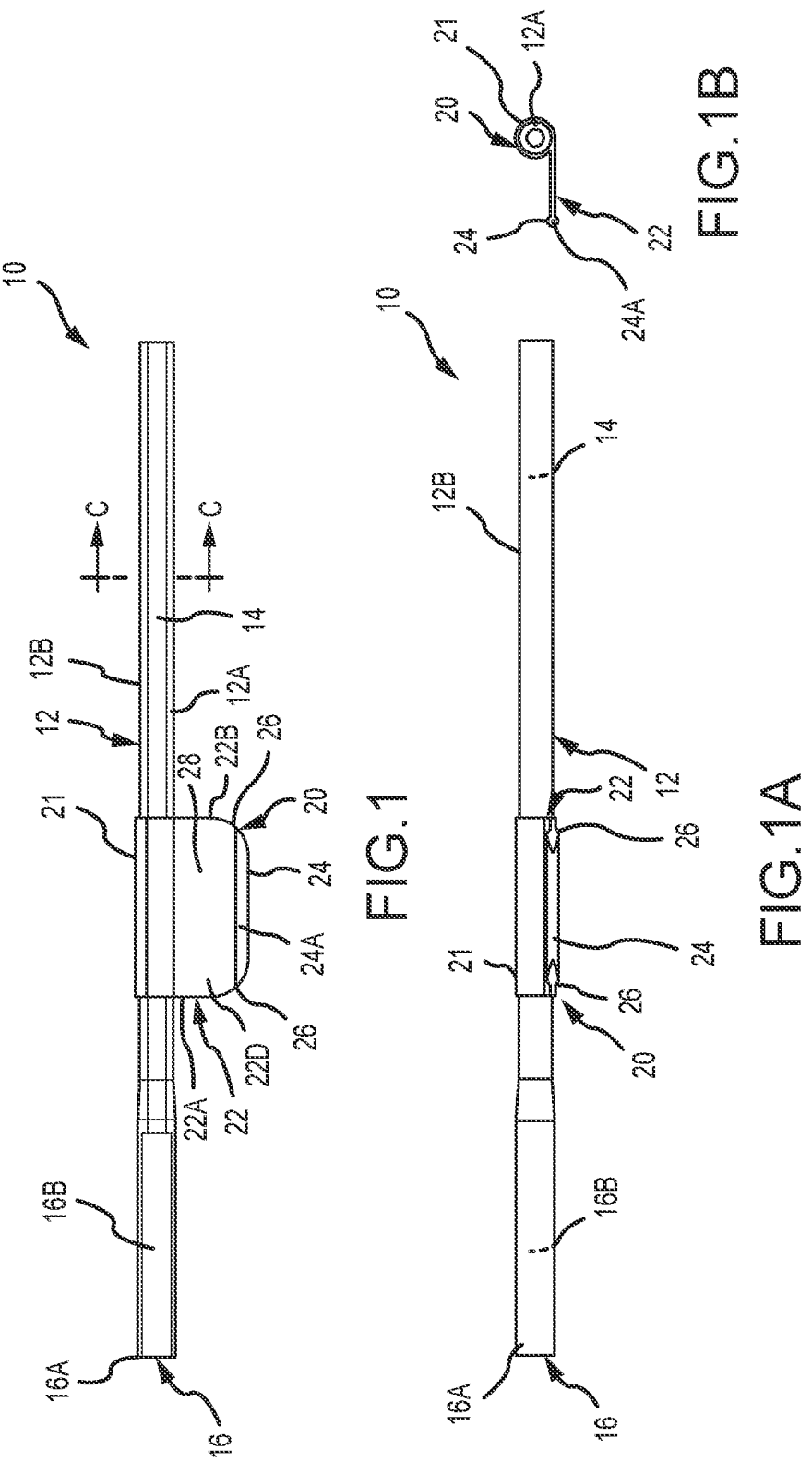

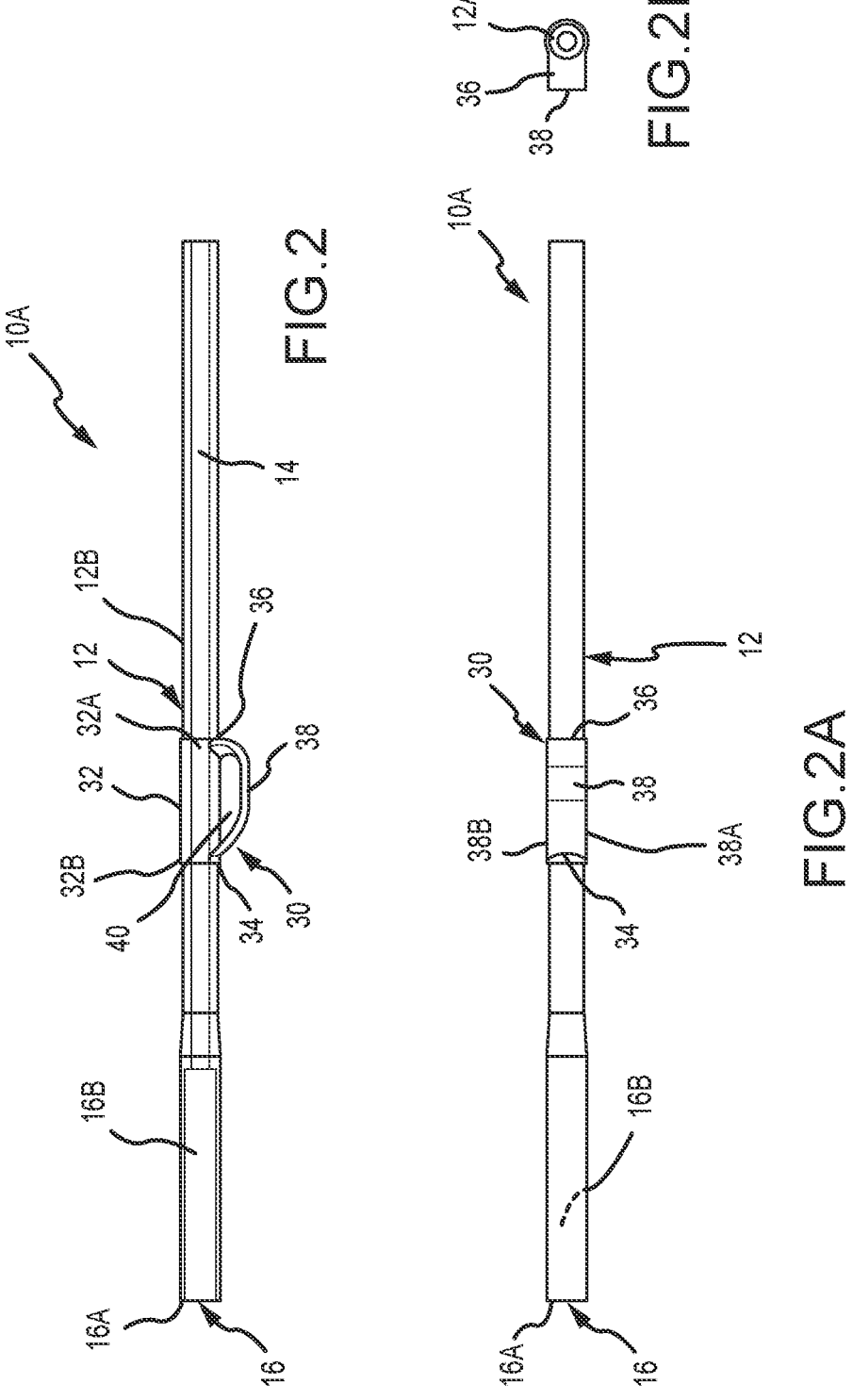

URINARY CATHETER WITH RETENTION FEATURES

CROSS REFERENCE TO RELATED APPLICATION

This application is a Continuation-in-Part of U.S. patent application Ser. No. 16/436,773, entitled "URINARY CATHETER," filed Jun. 10, 2019, which is incorporated herein by reference.

FIELD

This disclosure relates to an extended-use catheter with asymmetric retention features that enable it to be retained in the body for an extended time.

BACKGROUND

Many people suffer from lower urinary tract dysfunction, also known as neurogenic bladder. Neurogenic bladder can be defined as impaired urinary function due to neurological injury or disease, such as spinal cord injury (SCI). Some known methods for managing neurogenic bladder and other chronic urinary retention disorders are to drain the bladder using (a) intermittent catheterization (IC), or (b) indwelling Foley catheters. These methods, however, are associated with relatively high rates of urinary tract infection and genito-urinary (GU) injury, each of which diminishes a patient's quality of life. Furthermore, because some individuals with neurogenic bladder lack bladder sensation, and thus cannot accurately perceive bladder fullness, they are susceptible to bladder over-filling. This can result in urinary "accidents" and/or urinary reflux, and urinary reflux presents a risk of infection and tissue damage to the upper urinary tract.

To avoid these problems, individuals with neurogenic bladder on an IC program commonly rely on a timed catheterization schedule. This approach is imprecise and may lead to catheterization more frequently than necessary, which can increase the risk of infection and GU injury. Therefore, it is desirable to provide an improved urinary prosthesis that helps to alleviate one or all of the preceding problems.

This application incorporates by reference the following: U.S. application Ser. No. 17/080,828 to Herrera et al., entitled Urethral Measurement Catheter and filed on Oct. 26, 2020; U.S. application Ser. No. 15/072,345 to Herrera et al., entitled Extended-Use Valved Urinary Catheter, and filed on Mar. 16, 2016; PCT Application Serial No. PCT/US2016/014648, entitled Bladder Management Systems, and filed on Jan. 23, 2016; U.S. application Ser. No. 15/545,903 to Herrera et al., entitled Bladder Management System, and filed on Jul. 27, 2017; U.S. application Ser. No. 15/721,096 to Herrera et al., entitled Urinary Prosthesis Systems, and filed on Sep. 29, 2017; U.S. Pat. No. 9,775,698, entitled Urinary Prosthesis Systems; U.S. application Ser. No. 15/785,403 to Herrera, entitled Extended-Use Catheters, and filed on Oct. 16, 2017; U.S. application Ser. No. 15/785,405 to Derek Herrera entitled Catheter Mating Devices, and filed on Oct. 16, 2017; U.S. application Ser. No. 15/785,398 to Derek Herrera entitled Catheters and Catheter Mating Devices and Systems, and filed on Oct. 16, 2017.

SUMMARY

The present disclosure relates to devices, systems and methods for extended-use bladder management and controlling urinary function for humans or other animals. The disclosed devices, systems, and methods may be used for fluid flow control for other bodily organs as well, such as kidneys, or draining abscesses or fluids from a body.

An extended-use catheter as disclosed is configured for being retained inside of the body. The catheter can be used, for example, in the human male or human female urinary tract. When in use, its distal end, which is the end that is positioned inside of the user's (or "patient's") bladder is preferably positioned fully inside of, and retained in, the bladder and the remainder of the catheter is positioned in the urethra. In one embodiment, the catheter comprises an elongated tube (or "tube") having a wall with an outer surface, and a lumen through which fluid, such as urine, can pass. Positioned on, or formed as part of, the tube wall are at least two structures to help retain the catheter in the body of a user. One is a retainer configured to be positioned in the bulbar urethra when the catheter is properly positioned in the body and the other is a bladder retention structure (or "retention structure") configured to be positioned in the bladder when the catheter is properly positioned in the body.

The retention structure is juxtaposed the distal end of the catheter, is flexible and is comprised of a soft, flexible material, such as silicone rubber. The retention structure can be a structure having a flexible flat portion (also referred to as a "flap" or "wing") that has a first, compressed position (or "first position" or "compressed position") in which it is pressed against and may be at least partially wrapped around the tube, and a second, extended position (or "second position" or "extended position") in which it extends outwards from the tube and has a length as measured from where it connects to the tube body of about 2-6 times greater than the outer diameter of the tube, although any suitable length may be used. This retention structure also has an attachment portion with an aperture that fits over and retains part of the tube body, or alternatively the attachment portion can be overmolded onto the tube. The flap is in its second position where it extends outward from the tube when positioned in the bladder, and is configured to collapse to its first position when pulled through the penile urethra. The retention structure can be moved from the second, expanded position to the first, compressed position by applying sufficient force to push it into, or pull it out, the penile urethra.

Alternatively, the retention structure may have a handle shape with an opening. In this embodiment, the retention structure has an attachment portion with an aperture that fits over and retains part of the tube body, or alternatively the attachment portion can be overmolded onto the tube. The housing has a housing distal end juxtaposed the distal end of the housing and a housing proximal end that is farther from the distal end of the catheter. A handle-shaped portion has a first leg attached to the housing distal end and a second leg attached to the housing proximal end. A center portion is formed between the first leg and the second leg. This retention structure has a first, compressed position (or "first position" or "compressed position") in which the center portion is pressed close to or against the tube, and a second, extended position (or "second position" or "extended position") in which the center portion extends outwards from the tube about 2-6 times farther than the tube diameter, although any suitable distance would suffice.

The first leg, second leg, and center portion each have a thickness that is about 1-4 times the thickness of a wall of the tube, although any suitable thickness may suffice. An opening (or "window" or "space") is between the center portion, the first leg, the second leg, and the outer wall of the tube and the opening has a height as measured from the tube outer surface to the inner surface of the center position of about 2-4 times the outer diameter of the tube, although any suitable height would suffice. This retention structure is also comprised of a soft, flexible material such as silicone rubber. Each bladder retention structure is further configured to assist in keeping one or more of the aperture(s) at the distal end from pressing against the wall of the bladder, which could block or inhibit the flow of fluid into the apertures.

The catheter may also include a retainer positioned between the distal end and the proximal end of the tube. The retainer preferably has one of the same structures as the bladder retention structure, although the dimensions may be different because the retainer is positioned in the bulbar urethra when the catheter id deployed in a body. The retainer is configured to help maintain the distal end in the bladder until sufficient force is applied to remove the distal end from the bladder (e.g., a user pulls the catheter out of the body). Once in the bulbar urethra, the retainer extends outward to its extended position in order to secure the catheter in position with the retention structure in the bulbar urethra and the distal end of the tube in the bladder until a user removes the catheter from the body. The retainer is configured to move to its first, compressed position when moved through the penile urethra.

Further, any of the structures used on the distal end of the catheters shown in U.S. patent application Ser. No. 16/436, 773, entitled "URINARY CATHETER," could be used as a retention structure or retainer in a catheter according to this disclosure, although the dimensions may be altered.

A catheter according to this disclosure could be periodically inserted, removed, and replaced by the user without medical assistance or the aid of another individual, which is convenient and saves time and medical expense. Such a catheter could remain in the body for days or weeks without being removed, which alleviates the problem of catheterization multiple times per day.

The catheter may be configured to include one or more sensors, which may be on, inside of, or embedded in material forming the catheter, or partially or entirely within the lumen. The one or more sensors can be at any suitable location on the catheter, such as at a position where they are positioned in the bladder when the catheter is properly positioned in the lower urinary tract of a human male. The one or more sensors could collect any relevant data, such as fluid pressure in the bladder, pH level of fluid, temperature, volume of urine in the bladder, and/or amount of blood or bacteria in urine. The one or more sensors could communicate with other devices, such as CT scanners, ultrasound devices, x-ray machines, electronic data storage devices, computers, cell phones, the wireless controller, the catheter mating device and/or sensors placed in toilets or hospital beds. The data collected by the sensors could be stored, analyzed and/or transmitted by a device including software configured for these functions.

Because the catheter can remain in the body for long periods, a sensor on the catheter can gather and send data over the entire period the catheter is in the body, as opposed to gathering data only at a specific time, such as when a patent is at a doctor's office or hospital.

A catheter mating device configured to engage and move the catheter is also disclosed and may be part of a system according to aspects of the invention. The catheter mating device has a distal end and a proximal end. The distal end is configured to connect to the proximal end of the catheter, and includes an apparatus moveable between: (a) a first position, wherein the apparatus is retracted, and (b) a second position, wherein the apparatus is expanded. When in the first position, the apparatus is configured to fit into the lumen (or a mating chamber of the catheter) at the proximal end of the catheter. Once placed in the lumen, the apparatus can be moved to its second position, wherein the apparatus expands until it presses against and engages the wall of the lumen (or inner wall of the mating chamber). That connects the catheter mating device to the catheter, and the catheter can then be pushed into, or removed from a body structure, such as a bladder and urethra by, respectively, pushing or pulling the catheter mating device. Thus, the catheter mating device can be used to: (a) accurately place the catheter inside of a body, and/or (b) remove the catheter from a body.

As used herein, the term "user" means any person able to insert and/or remove a catheter as disclosed herein, and includes a patient, doctor, caregiver, and nurse. "Patient" means a person that uses a catheter as disclosed herein in his/her body. "Lower urinary tract" refers collectively to the urinary bladder and urethra. "Extended use" means a catheter that can be used without having to remove it from the body more than once every two days or longer.

BRIEF DESCRIPTION OF THE DRAWINGS

FIG. 1 is a partial, top view of an exemplary urinary catheter with a retainer in an extended position.

FIG. 1A is a side view of the partial urinary catheter of FIG. 1.

FIG. 1B is an end view of the urinary catheter of FIG. 1A.

FIG. 2 is a partial, top view of a catheter according to this disclosure with an alternate retainer.

FIG. 2A is a top view of the partial catheter of FIG. 2.

FIG. 2B is an end view of the partial catheter of FIG. 2A.

DETAILED DESCRIPTION OF PREFERRED EMBODIMENTS

Extended-Use Catheter

Figure 1C:
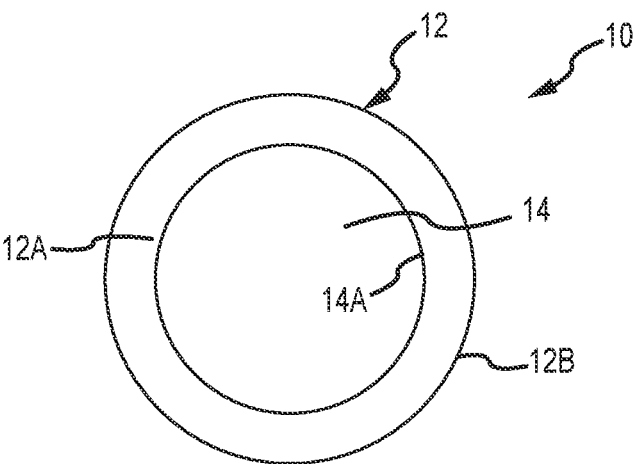
FIG. 1C is a cross-sectional view of the tube of the urinary catheter of FIG. 1 taken along lines C-C.
Figure 1G:
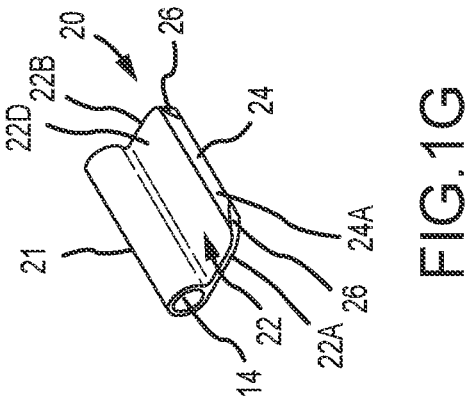
FIG. 1G is a side, perspective view of the retainer of FIG. 1D.
Figure 1D:
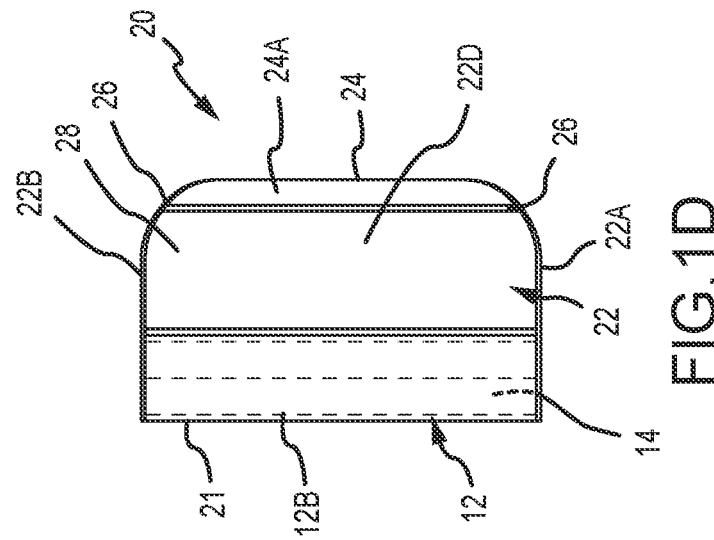
FIG. 1D is a top view of the retainer of FIG. 1.
Figure 1E:
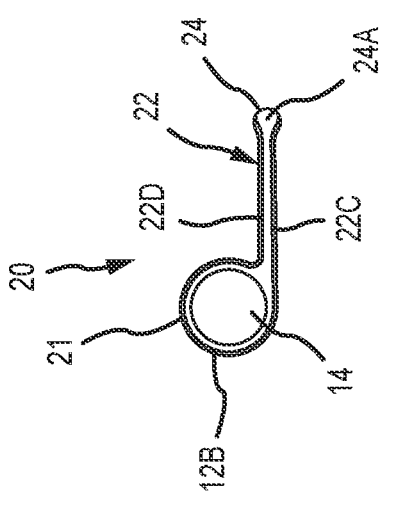
FIG. 1E is an end view of the retainer of FIG. 1D.
Figure 1F:
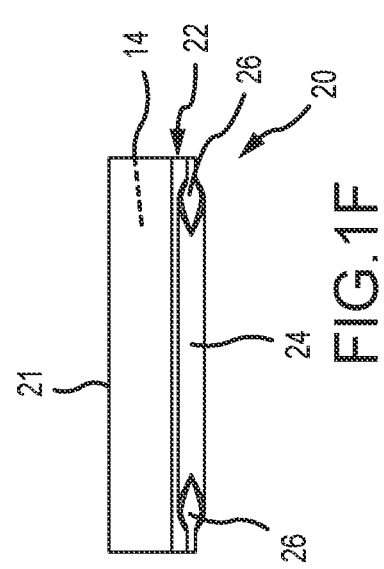
FIG. 1F is a side view of the retainer of FIG. 1D.
Figures 3, 4:
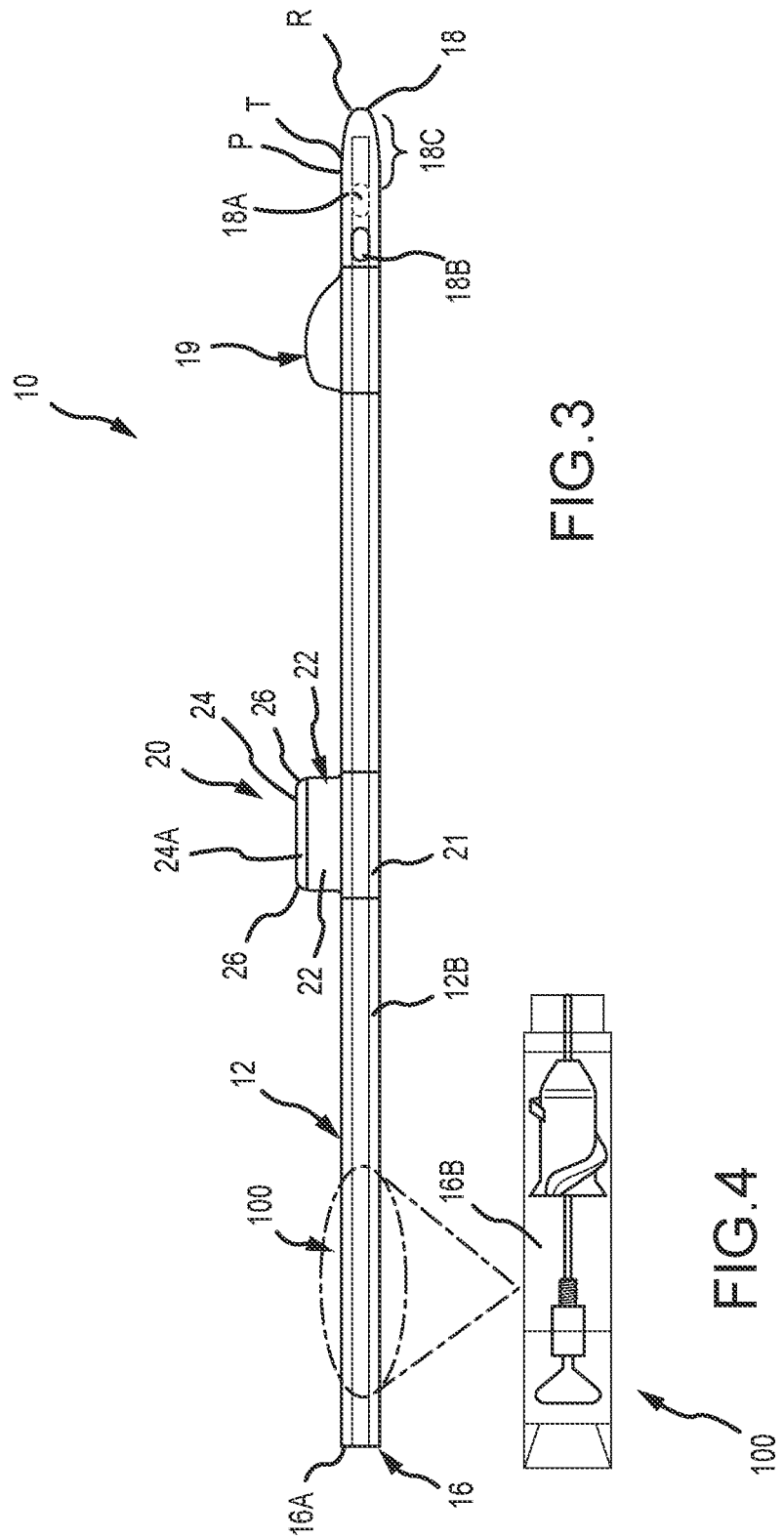
FIG. 3 is a side view of a catheter according to this disclosure.
FIG. 4 is an enlarged, side view of a valve according to this disclosure positioned inside the catheter of FIG. 3.
Figure 9:
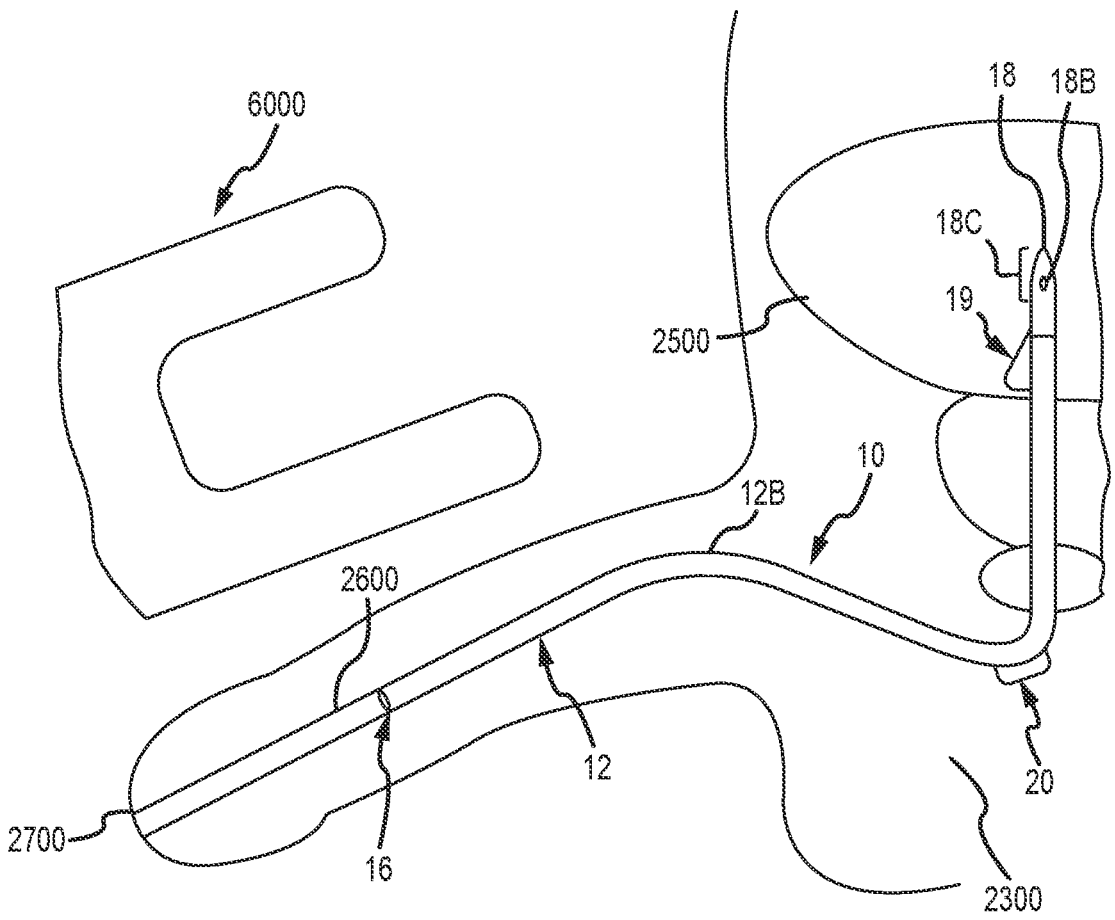
FIG. 9 shows the urinary catheter of FIG. 3 positioned in the lower urinary tract of a human male.

Turning now to the Figures, wherein the purpose is to describe preferred embodiments and not to limit the scope of the invention, FIGS. 1-1G and 3 show an exemplary catheter 10 according to aspects of the invention. Catheter 10 is an extended use catheter, and can be shaped and sized to be introduced into, and retained in, the lower urinary tract of a human male or human female. As shown in FIG. 9, catheter 10 can extend from the bladder 2050 to a portion of the urethra 2600 distal to the prostate and distal to the bulbar urethra. Catheter 10 as shown in FIG. 9 extends past the prostate and the external urinary sphincter. In a female anatomy, the retainer 20 is preferably positioned within the urethra, between the internal urethral orifice and the external urethral orifice. The retainer 20 can then be positioned such that it is in the bulbar urethra between the meatus and the external urethral sphincter with the retention structure and distal end positioned in the bladder. Catheter 10 is preferably fully internal to the body once properly installed.

Turning to FIGS. 1-1C, and 3-4, catheter 10 can comprise a tube 12 with a wall 12A having an outer surface 12B, a lumen 14 with a lumen wall 14A, a valve 100, a retainer 20, a proximal end 16 with a proximal tip 16A and an engagement chamber 16B, and a distal end 18 with bladder retention structure 19, and openings 18A and 18B. The catheter tube 12, which is shown in cross section in FIG. 1C, preferably has a circular cross-sectional shape, but can be of any shape suitable for the intended use of catheter 10. In one embodiment tube wall 12A has a thickness of about 0.45 mm, or from about 0.35 mm to about 0.55 mm.

When used in the lower urinary tract of a human male, as shown in FIG. 9, tube 12 preferably has an outer diameter (as measured across outer surface 12B) ranging from about 1 French (0.3 mm) to 20 French (6.6 mm), which is approximately the same as or less than the maximum expanded dimension of the urethra 2600. Wall 12A can have a hardness of any amount from: about 30 Shore A to 55 Shore D, or about 60 Shore A, or about 30 to 70 Shore A, or about 20 to 50 Shore A, although any suitable hardness for the intended use of catheter 10 would suffice.

Lumen 14 may have any suitable cross-sectional geometrical shape (e.g., circular (which is most preferred), oval, semi-circular, rectangular, triangular, trapezoidal, or crescent) and can have a cross-sectional surface area (which is the area inside of lumen wall 14A when viewed in cross section) equivalent to the area of a 0.1 mm diameter circle to that of a 5.5 mm diameter circle. If the cross-sectional shape of lumen 14 is circular lumen 14 preferably has a diameter of any amount from: 0.1 mm to 5.5 mm. Lumen 14 may also comprise different cross-sectional areas along its length. For example, the cross-sectional area of the lumen may be greater where the valve 100 is positioned, and/or a greater cross-sectional area at the proximal end 16. Or the lumen's cross-sectional area may be greater along its entire length distal to valve 100.

Figure 10:
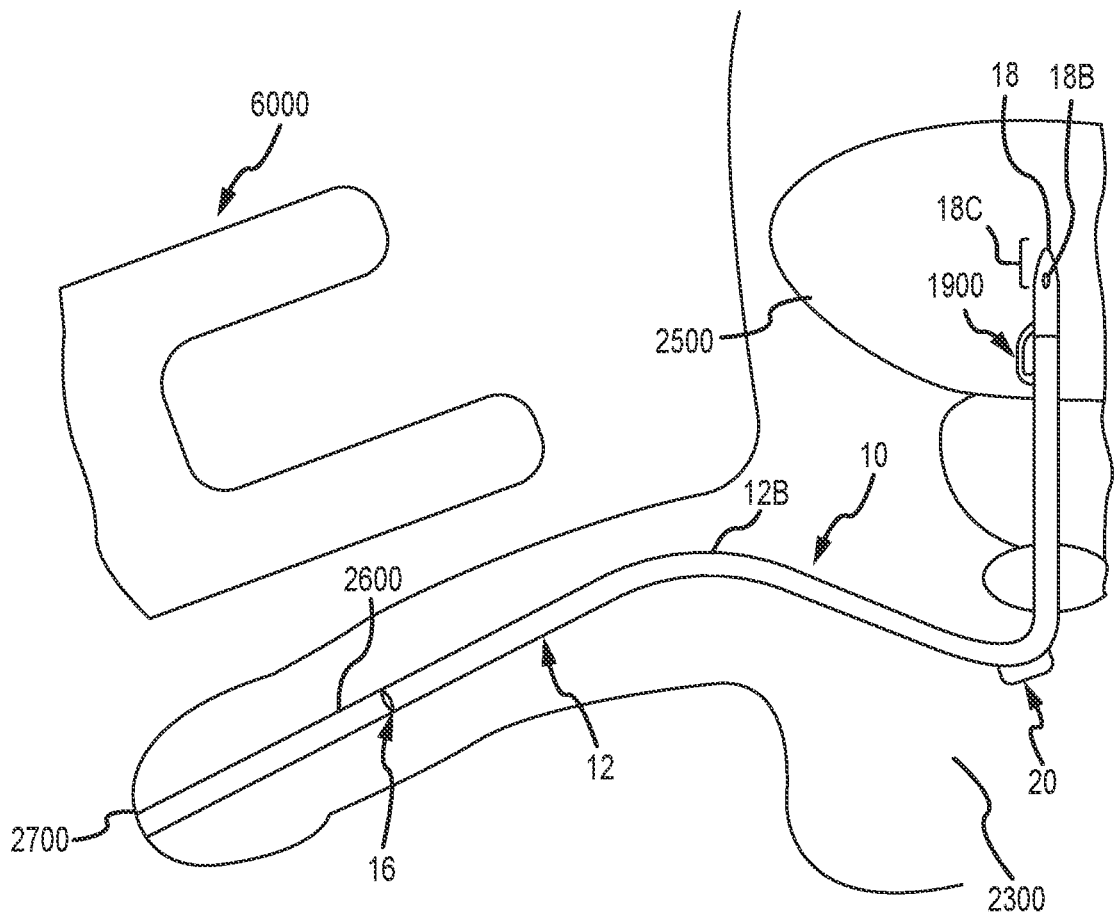
FIG. 10 shows the urinary catheter of FIGS. 1-1B with the distal end of FIGS. 5-8 positioned in the lower urinary tract of a human male.
Figure 11:
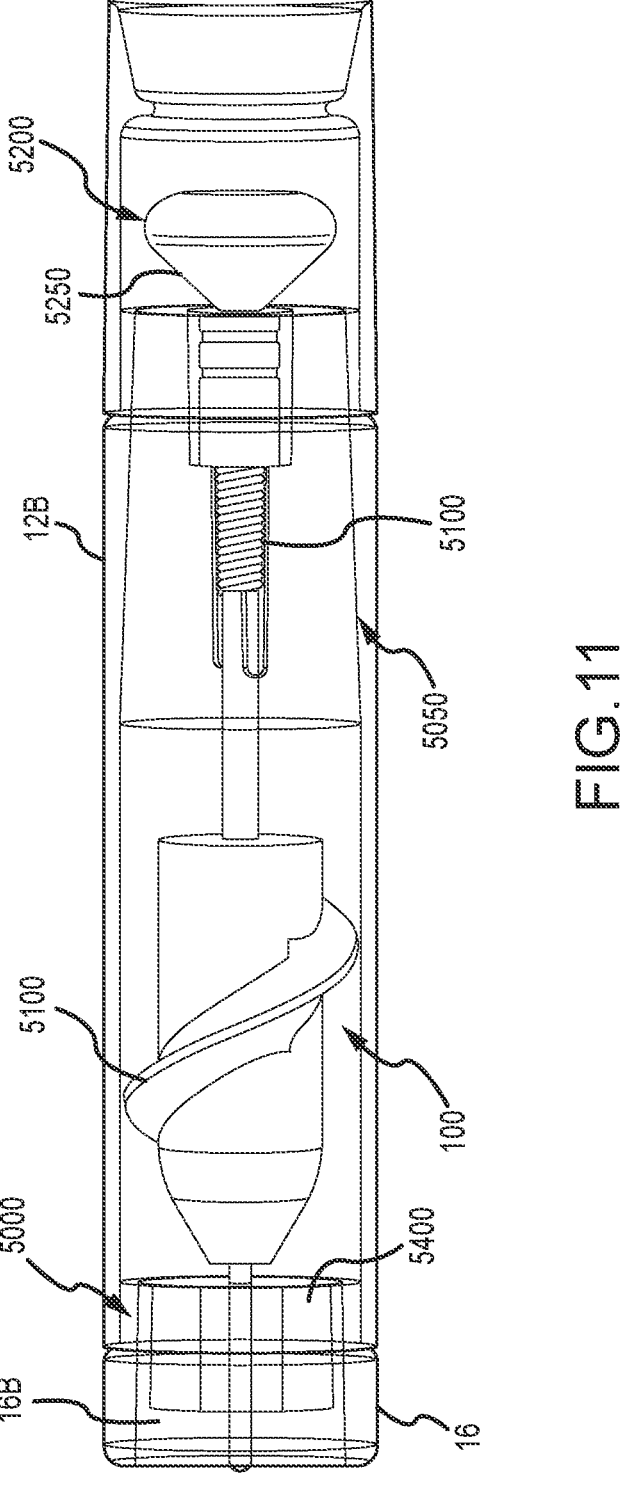
FIG. 11 is a close-up, partial, open view of the proximal end of the urinary catheter of FIG. 1 showing a valve.
Figure 12:
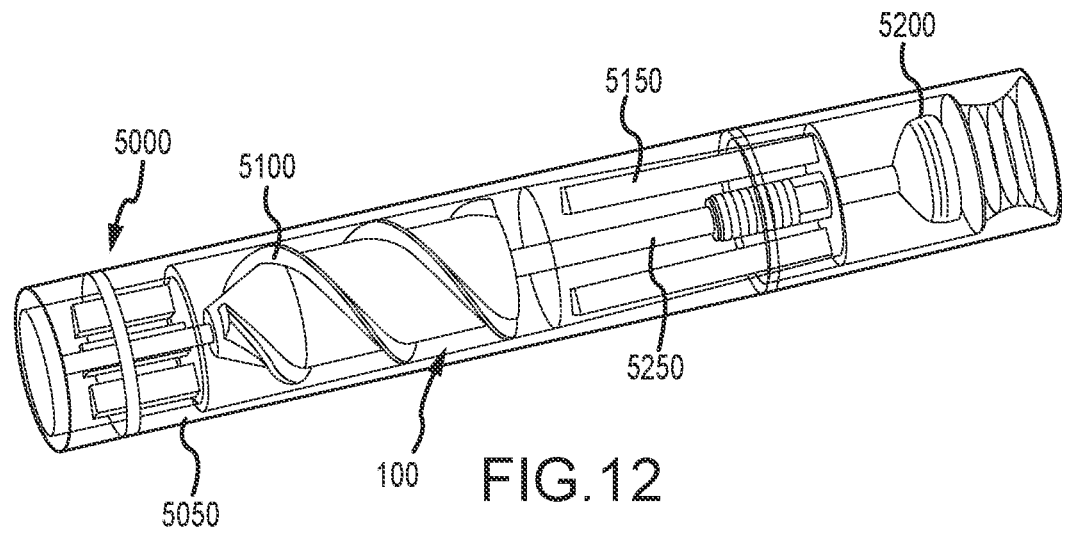
FIGS. 12-12B show the valve of FIG. 11 and components of the valve.
Figure 12A:
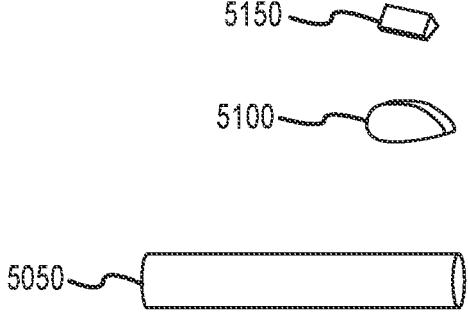
Figure 12B:
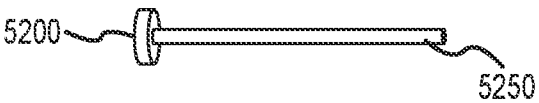

Tip 16A can have an outer diameter larger or smaller than the diameter of the outer wall 12B. For example, tip 16A may have a diameter of 0.5 mm-1 mm larger or smaller than the diameter of outer wall 12B. The purpose of tip 16A having a slightly different diameter is so a user can locate it by touch (e.g., by pressing against the skin and feeling the ridge at tip 16A) when tip 16A is positioned in the penile urethra, as shown in FIGS. 9-10.

Engagement chamber 16B can be at or near the proximal end 16 of the catheter 10. The engagement chamber 16B can be located between the proximal tip 16A and the valve 100, or extend from proximal tip 16A to the most distal portion of valve 100 and retain valve 100. The engagement chamber 16B includes a space configured to engage an apparatus 1172, which is described below. The engagement chamber 16B can have an annular, cylindrical shape, with a circular cross-section although any suitable shape may be used. As shown, the engagement chamber 16B has a circular cross-sectional shape with a diameter preferably form 0.1 mm to 5.5 mm. The engagement chamber 16B may have a hardness greater than the hardness of tube 12. For example, the hardness may be of any hardness between 10 Shore A to 55 Shore D harder than tube 12, or 10 Shore A-20 Shore A or harder, or 20 Shore A-50 Shore A or harder, or 50 Shore A-55 Shore D or harder. A purpose for engagement chamber 16B being harder than tube 12 is to better secure apparatus 1172 in engagement chamber 16B. It is not, however, required that catheter 10 have a mating chamber 16B or that mating chamber 16B be harder than the rest of tube 12. For example, apparatus 1172 could engage lumen wall 14A or another structure.

As shown, for example, in FIGS. 3, 5-6, and 9-10, distal end 18 is configured to enter the patient's body through the urethral orifice 2700, and into the urethra 2600 when catheter 10 is positioned inside the lower urinary tract, and is finally positioned in the bladder. As shown in this embodiment, distal end 18 has a bullet-shaped tip 18C that is tapered, rounded and closed. The distal tip 18C can comprise a material with hardness greater than the hardness of wall 12A, such as a hardness of 10% greater, 20% greater, 30% greater, 40% greater, 50% greater, 50-100% greater, or 20-100% greater. Tip 18C narrows from an annular proximal part P to a rounded end R. It has an intermediate, tapered portion T that reduces in cross-sectional area from about 5% to 20% from proximal part P before reaching rounded end R.

Distal end 18 permits the inflow of bodily fluid, such as urine, from a bladder or other body part into lumen 14, which can be accomplished in any suitable manner. As shown one or more (and preferably, two) openings 18A and 18B permit bodily fluid, such as urine, to enter lumen 14. As shown, openings 18A and 18B are on opposite sides of tube 12, so if one opening 18A or 18B is blocked because it is positioned against body tissue, the other opening 18A or 18B should still be unblocked. However, there need only be one opening, or there could be more than two openings at distal end 18, and the openings could be of any suitable size, configuration or location so they allow fluid, such as urine from the bladder, to enter lumen 14.

When catheter 10 is positioned in the lower urinary tract of a human male, the one or more openings 18A and 18B are positioned in the bladder 2500, as shown in FIGS. 9 and 10. Retainer Retainer 20, shown in Figures is positioned between the distal end 18 and the proximal end 16. The retainer 20 is positioned in the bulbar urethra 2300 when catheter 10 is properly positioned in the lower urinary tract of a human male, as shown in FIGS. 9 and 10. Retainer 20 is configured to help prevent the inadvertent migration of catheter 10 either forward or backward once catheter 10 is properly positioned in the body. When positioned in the bulbar urethra, the retainer 20 is blocked by the external sphincter to prevent inadvertent retrograde migration, and blocked by the penile portion of the urethra 2600 to prevent inadvertent ante grade migration. When sufficient pulling or pushing force is applied to catheter 10, retainer 20 compresses from its second, expanded position, in which it is extended from outer surface 12B of tube 12, as shown, for example, in FIGS. 1-1B, 1D-1G, 3, and 9, to its first, compressed position, in which it is pressed against the outer wall 12B of tube 12, so that it can pass through the penile portion of the urethra 2600. In this manner, catheter 10 can be removed from, or be placed in, the lower urinary tract. The retainer 20 may be of suitable thickness, length, and hardness suitable for use of the catheter 10.

The retainer 20 as shown comprises a connecting (or attachment) portion 21, which fits over, is overmolded, or is otherwise attached to outer wall 12B of tube 12, and a flap (or "wing" or "structure") 22. Flap 22 preferably has a length (as measured from the position where it connects to outer wall 12B of tube 12 to the outermost edge 24) that is about 20%, or about 30%, or about 40%, or about 50%, or about 60%, or about 70%, or about 80%, or about 90%, or about 100%, or about 120%, or about 150%, or any amount from 20%-50%, 30%-75%, 40%-100%, 100%-150%, or 100%-500%, or 200%-500%, or 300% to 600%, or 300% to 800%, of the diameter of the tube 12. In one exemplary embodiment, the overall length of retainer 20 (including the diameter of tube 12) is about 18.3 mm, or between 15 mm-25 mm.

Retainer 20 preferably has a thickness as measured from flat side 22C to flat side 22D that is about 10%, about 20%, about 30%, about 40%, about 50%, about 60%, about 70%, about 80%, about 90%, about 100%, about 110%, about 120%, about 130%, about 1540%, about 150%, or any amount from 10% to 150% of the thickness of the tube wall, as measured from outer surface 12B to lumen wall 14A. The thickness could be between 0.75 mm to 1.0 mm or about 0.085 mm.

Retainer 20 could have a 70A shore hardness with a 0.85 mm wall thickness as measured along from side 22C to side 22D.

Retainer 20 has an axial length as measured from side 22A to side 22B along attachment portion 21 that can be about equal to the length (referenced above), or any amount from about 50% of the length to about 200% of the length, such as about 10%, about 20%, about 30%, about 40%, about 50%, about 60%, about 70%, about 80%, about 90%, about 100%, about 110%, about 120%, about 130%, about 1540%, about 150% about 160%, about 170%, about 180%, about 190%, or about 200%. In one embodiment the axial length is about 30 mm, or from about 25 mm to about 35 mm.

The retainer 20 may comprise a thicker portion, or thicker ridge (shown as a cylindrical bulb) 24A along outer edge 24 as compared to the thickness of the rest of flap 22. For example, the thickness of bulb 24A could be thicker than the thickness as measured between surface 22C and 22D by any amount from 10% to 100%, such as 10%, 20%, 30%, 40%, 50%, 60%, 70%, 80%, 90%, or 100% thicker. This added thickness at edge 24 can aid in collapsing the retainer for insertion, also provide additional rigidity to support proper anchoring, and also provide a smooth surface to alleviate trauma.

The average retention force of catheter 10 (after it has been properly positioned in the bladder of an adult, human male) according to this disclosure in the forward direction (i.e., into the bladder) is about 0.5 lbs. to 1.0 lbs., 1.15 lbs. to 1.5 lbs., or about 1.15 lbs. to 1.70 lbs. The average retention force of catheter 10 (after it has been properly positioned in the bladder of an adult, human male) according to this disclosure in the reverse direction (i.e., outward from the bladder) is about: 0.5 lbs., to 1.0 lbs., 1.0 lbs. to 1.5 lbs., 1.30 lbs. to about 2.0 lbs., or about 1.3 lbs. to about 2.0 lbs., or about 1.3 lbs. to about 1.8 lbs.

The retainer 20 should be atraumatic, and it preferably is comprised of a flexible silicone, or other suitable material. When used in the lower urinary tract of a human male, the retainer 20 should compress to at least a dimension so that it can be pushed or pulled through the maximum expanded dimension of urethra 2600, which could be a diameter of about 6 mm to 12 mm, or about 10 mm. The retainer 20 expands once it is no longer restricted. When used in the lower urinary tract of a human male, the retainer 20 moves to its first, compressed position when it is pulled through urethra 2600 and expands to its second, expanded once it enters the bulbar urethra 2300.

The retainer 20 is compressed to its first, compressed position when a total force is applied to it of about 0.1 lbs., 0.25 lbs., 0.1 lbs.-0.25 lbs., 0.05 lbs.-0.1 lbs., or 0.1 lbs.-0.2 lbs., 0.5 lbs., to 1.0 lbs., 1.0 lbs. to 1.5 lbs., 1.30 lbs. to 2.0 lbs., about 1.5 lbs. to about 2.2 lbs., or about 1.3 lbs. to about 1.8 lbs.

Figures 2C, 2D, 2E, 2F, 2G:
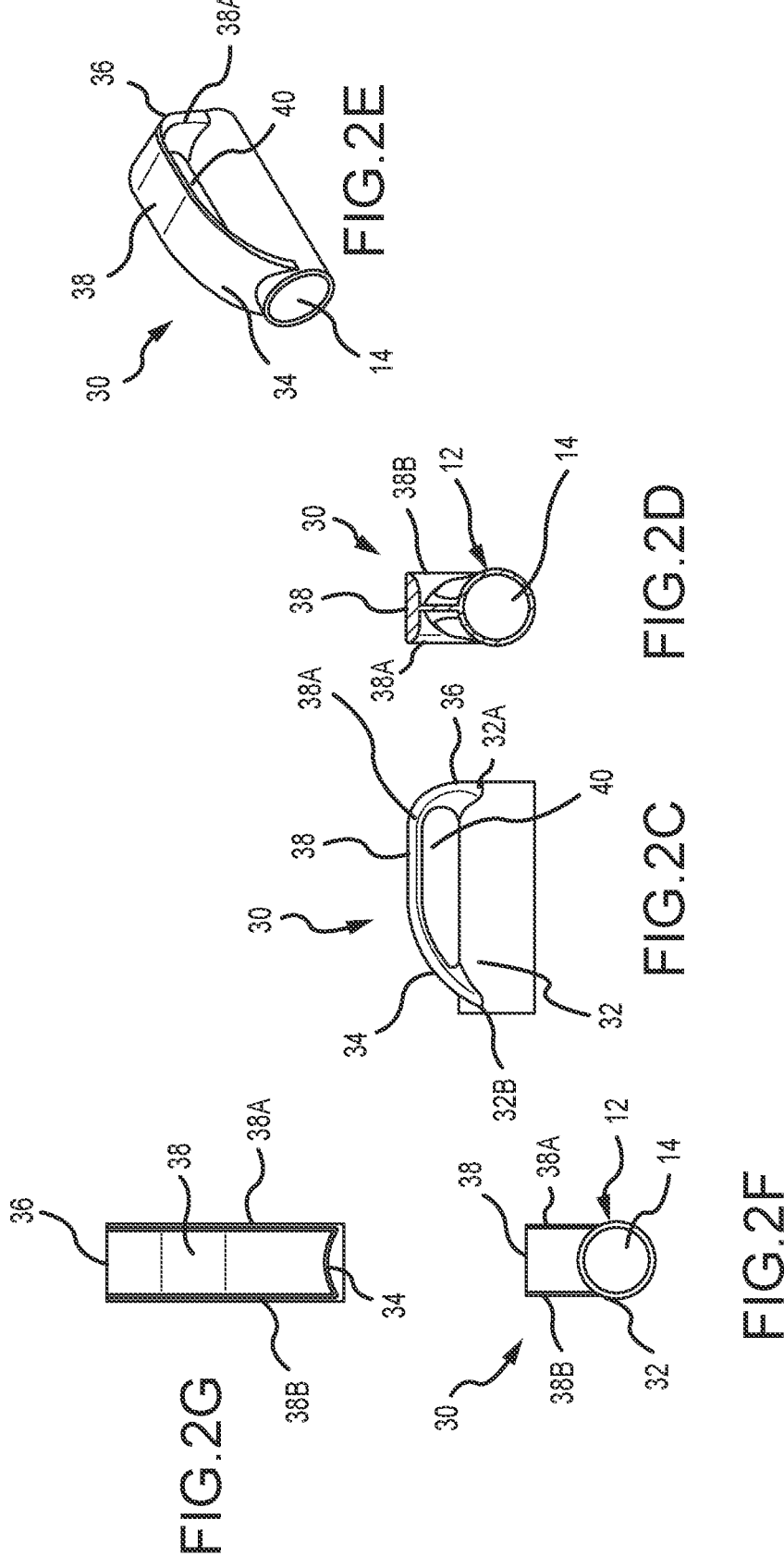
FIG. 2C is a partial, close up, bottom view of the catheter and retainer of FIG. 2.
FIG. 2D is an end view of the catheter and retainer of FIG. 2C.
FIG. 2E is a side, perspective view of the catheter and retainer of FIG. 2C.
FIG. 2F is an end view of the catheter and retainer of FIG. 2C.
FIG. 2G is a top view of the catheter and retainer of FIG. 2C.
Figure 21:
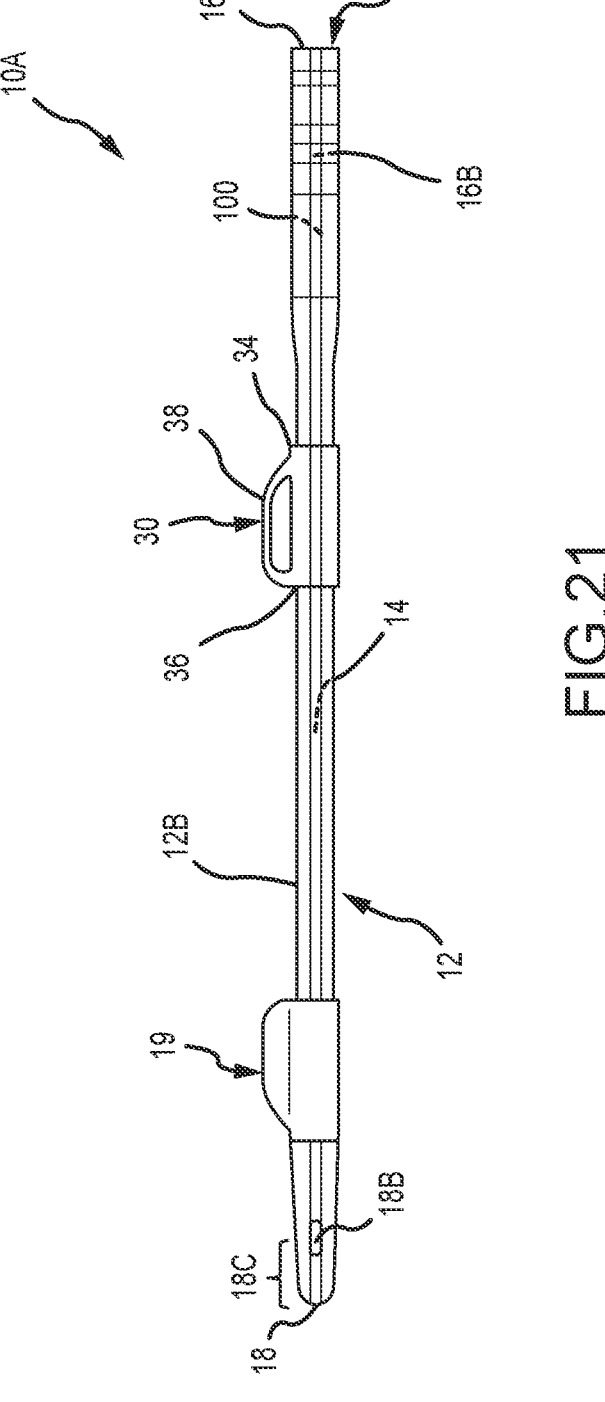
FIG. 21 is a complete, side view of the catheter of FIG. 2.

Another retainer 30 is shown in FIGS. 2-2G and 21 for catheter 10A. This retainer 30 is handle-shaped and has an attachment portion 32 connected (or attached) to tube wall 12B. Attachment portion 32 can be cylindrical and hollow and be positioned over tube 12, be overmolded onto tube 12, or otherwise attached to tube 12. Retainer 30 has a first, compressed position in which at least part of it presses against tube wall 12B and a second, expanded position in which it is unconstrained and expands outwards, as shown, for example, in FIG. 2. The retainer 20 may be compressed to its first, compressed position when a total force is applied to it of about 0.1 lbs., 0.25 lbs., 0.1 lbs.-0.25 lbs., 0.05 lbs.-0.1 lbs., or 0.1 lbs.-0.2 lbs., 0.5 lbs., to 1.0 lbs., 1.0 lbs. to 1.5 lbs., 1.30 lbs. to 2.0 lbs., about 1.5 lbs. to about 2.2 lbs., or about 1.3 lbs. to about 1.8 lbs.

Attachment portion 32 has an axial length that is about 20 mm, but could be of any suitable amount, which as about 10 mm to 30 mm, which is preferably the same as the length of retainer 30 as measured along the longitudinal axis of catheter 10. Attachment portion 32 has a distal side 32A and a proximal side 32B.

Retainer 30 has a first leg 34 that is connected to or formed with proximal side 32B. As shown leg 34 has a backward curvature towards the distal end of catheter 10. Leg 34 continues along a curve until it reaches essentially flat, straight center portion 38. Straight center portion 38 then connects to, or is formed with, Second leg 36, which as shown is curved downwards until it connects with distal side 32A of attachment portion 32. Retainer 30 has a first side 38A and a second side 38B.

An opening (or "window" or "space") 40 is between first leg 34, center portion 38, second leg 36, and attachment portion 32 (or tube 12).

The entire height of retainer 30 could be about 11 mm including the thickness of tube 12, or about 10-15 mm, or any suitable amount. The width of legs 34 and 36, and of center portion 38, could be about 5.7 mm, or from about 4 mm to about 6.5 mm.

Figures 22, 23:
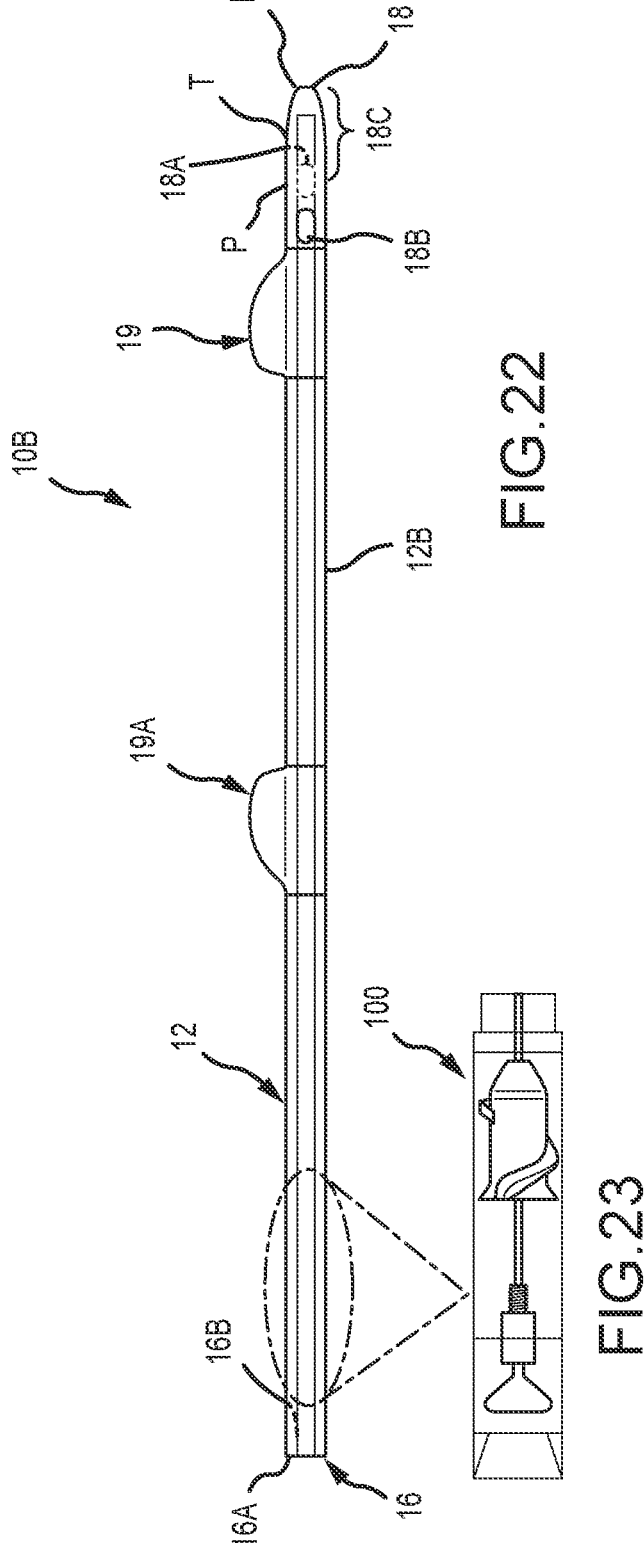
FIG. 22 is side vie of an alternate embodiment of a catheter according to this disclosure.
FIG. 23 is a side view of a valve 100 used with the catheter of FIG. 22.

The urinary catheter may comprise a retainer 19A, as shown in FIG. 22 (for catheter 10B). This retainer 1 A may have one of the structures disclosed in U.S. patent application Ser. No. 16/436,773, entitled "URINARY CATHETER," filed Jun. 10, 2019, which is incorporated herein by reference.

Bladder Retention Structure

The urinary catheter may comprise an bladder retention structure 19 on the distal end 18, as shown in FIGS. 1I, 1J, 2, 21 (for catheter 10A) and 22 (for catheter 10B). The bladder retention structure 19 may have the same structure as described above for retainer 20 or have one of the structures disclosed in U.S. patent application Ser. No. 16/436,773, entitled "URINARY CATHETER," filed Jun. 10, 2019, which is incorporated herein by reference.

Another retention structure 1900 is shown in FIGS. 5-8. This retention structure 1900 is handle-shaped and has an attachment portion 1932 connected (or attached) to tube wall 12B. Attachment portion 1932 can be cylindrical and hollow and be positioned over tube 12, be overmolded onto tube 12, or otherwise attached to tube 12. Retention structure 1900 has a first, compressed position in which at least part of it presses against tube wall 12B and a second, expanded position in which it is unconstrained and expands outwards, as shown, for example, in FIG. 2. The retention structure 1900 may be compressed to its first, compressed position when a total force is applied to it of about 0.1 lbs., 0.25 lbs., 0.1 lbs.-0.25 lbs., 0.05 lbs.-0.1 lbs., or 0.1 lbs.-0.2 lbs., 0.5 lbs., to 1.0 lbs., 1.0 lbs. to 1.5 lbs., 1.30 lbs. to 2.0 lbs., about 1.5 lbs. to about 2.2 lbs., or about 1.3 lbs. to about 1.8 lbs.

Attachment portion 1932 has an axial length that is about 20 mm, but could be of any suitable amount, which is about 10 mm to 30 mm, which is preferably the same as the length of retention structure 1900 as measured along the longitudinal axis of catheter 10. Attachment portion 1932 has a distal side 1932A and a proximal side 1932B.

Retention structure 1900 has a first leg 1934 that is connected to or formed in proximal side 1932B. As shown leg 1934 has a backward curvature towards the distal end of catheter 10. Leg 1934 continues along a curve until it reaches essentially flat, straight center portion 1938. Straight center portion 1938 then connects to, or is formed with, second leg 1936, which as shown is curved downwards until it connects with distal side 1932A of attachment portion 1932. Retention structure 1900 has a first side 1938A and a second side 1938B.

An opening (or "window" or "space") 1940 is between first leg 1934, center portion 1938, second leg 1936, and attachment portion 1932 (or tube 12).

The entire height of retention structure 1900 could be about 11 mm including the thickness of tube 12, or about 10-15 mm, or any suitable amount. The width of legs 1934 and 1936, and of center portion 1938, could be about 5.7 mm, or from about 4 mm to about 6.5 mm.

Valve

The valve 100 is preferably configured to restrict, or allow, fluid flow from the bladder 2000 (or other body part) out of the proximal end 16 of catheter 10. In the embodiment shown, the valve 100 is located in lumen 14 between the proximal end 16 and the retention structure 20, although the valve 100 can be positioned at any suitable location in the lumen 14, or at the distal end 18 or proximal end 16 of catheter 10, as long as the valve can open to allow, and close to prevent fluid flow out of proximal end 16. As shown in this embodiment, the valve 100 is a magnetic valve, and wireless controller 6000 (described below) can be placed on or near valve 100 from outside of the patient's body to operate valve 100.

The valve 100 preferably comprises a cylindrical body. As shown in FIG. 4, the valve 100 includes a housing 5050, a screw portion 5100, a valve magnet 5150, a valve tip 5200, a spindle 5250, and an alignment tube 5300. The housing 5050 can comprise a cylindrical body. The screw portion 5100 can comprise a threaded body. The valve tip 5200 can be connected to the spindle 5250. The valve tip 5200 can be configured to open and close the valve. For example, the valve tip 5200 can comprise a conical surface corresponding to a seating structure of the valve opening 5400.

The screw portion 5100 can be movable inside the housing 5050. The housing 5050 and the screw portion 5100 can be in a threaded connection. The magnet can be connected to the screw portion 5100 and the spindle 5250. By moving the magnet 5150, the valve 100 can open and close. For example, the magnet 5150 can be moved by using an wireless controller 6000 (described below) to open and close the valve 100, such as by spinning magnet 5150, in order to activate the valve 100 and facilitate and/or control fluid flow. The valve 100 and the wireless controller 6000 can be configured to allow the user to increase or decrease the flow rate of the urine from the bladder 2500 by the wireless controller 6000 signaling the valve 100.

If valve 100 is a magnetic valve, as shown in this embodiment, when it is operated it pumps fluid, rather than simply allowing fluid to flow as a result of fluid pressure in the bladder 2500 or other body structure in which distal end 18 is positioned. Using the bladder 2500 as an example, by pumping fluid the bladder is more completely emptied, which can lead to relieving the bladder fewer times over a given period of time. Alternatively, the valve could be any structure that can be operated to (a) prevent the passage of fluid out of proximal end 16, and (b) allow fluid to flow past proximal end 16.

Catheter Mating Device

A system according to the invention can comprise a catheter 10 and a catheter mating device 1000, wherein the catheter mating device 1000 and catheter 10 are each configured to connect to one another so that catheter 10 can be moved by moving the catheter mating device 1000. As shown in FIGS. 14-20, the catheter mating device 1000 can be used to place the catheter 10 into a patient's body, and to remove the catheter 10 from the patient's body. The catheter mating device 1000 comprises a stem 1150 that includes: (a) a tube 1152 having an outer surface (or external wall) 1154 and a lumen 1162, (b) an inner cylinder 1160 having a distal end 1160A and a proximal end 1160B connected to a control 1520, and (c) a distal end 1170 with apparatus 1172.

The apparatus 1172 is a structure that operates mechanically to connect the stem to the proximal end of the catheter, thus connecting the catheter mating device 100 to catheter 10. Apparatus 1172 has a first, retracted position, wherein it can fit inside of the proximal end 16 of tube 12, and a second, expanded position, wherein it engages proximal end 16 and connects catheter mating device 100 to catheter 10.

Figures 5, 6, 7, 8:
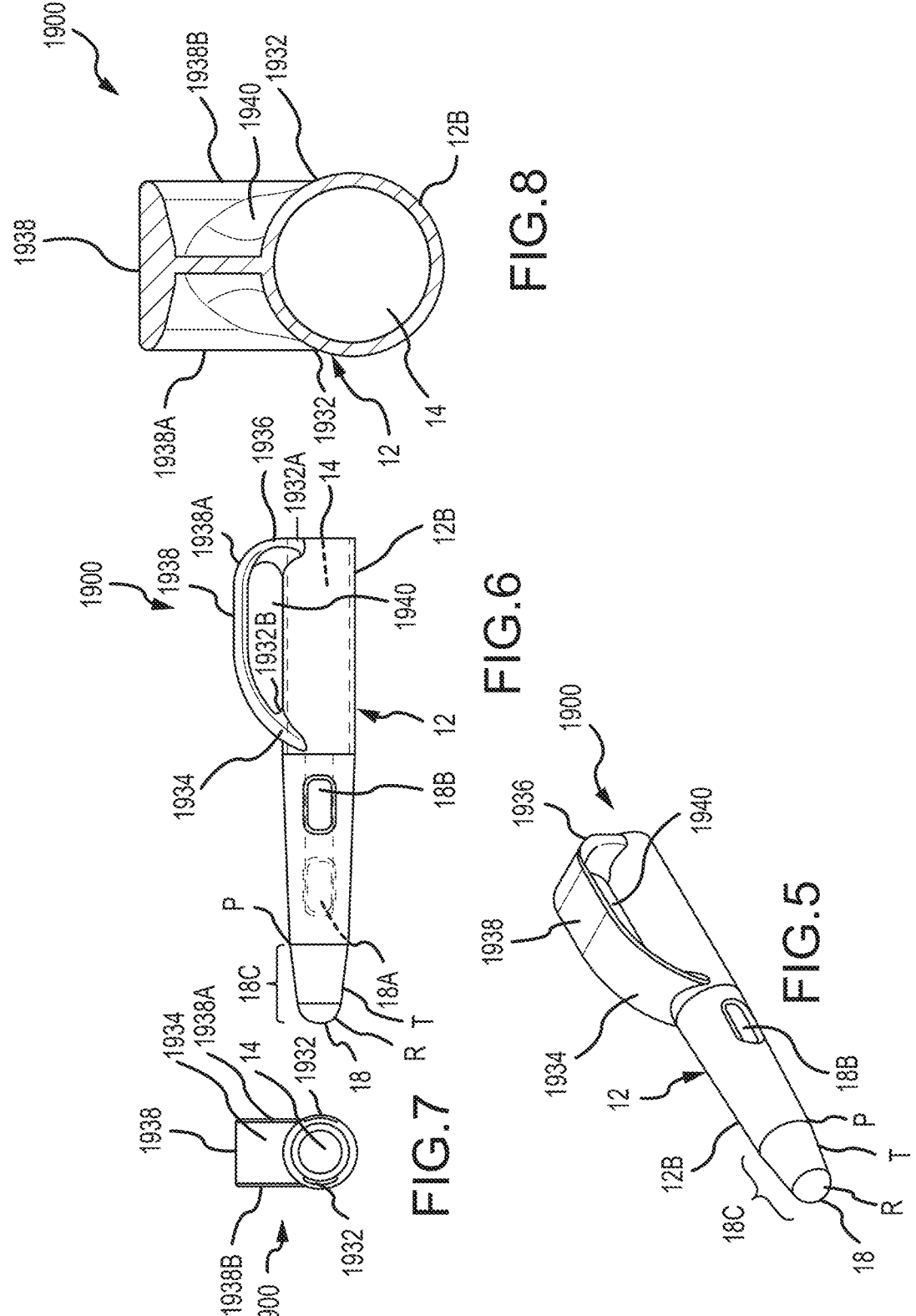
FIG. 5 is a partial, side perspective view of a distal end of a catheter according to this disclosure.
FIG. 6 is a side, partial phantom view of the catheter distal end of FIG. 5.
FIG. 7 is an end view of the catheter distal end of FIG. 6.
FIG. 8 is a cross-sectional view of the catheter distal end of FIG. 6 taken through line A-A.

The apparatus 1172 comprises tips 1174 that are configured to be positioned inside proximal end 16 (such as inside of engagement chamber 16B) when tips 1174 are in their first, retracted position and have a first distance between them (which may be zero distance because tips 1174 may touch when in the first, retracted position) as best seen in FIGS. 8-8D. Tips 1174 can be moved to their second, expanded position in which they have a second distance between them that is larger than the first distance. In the second, expanded position, tips 1174 engage the inner wall of engagement chamber 16B, which connects catheter 10 to catheter mating device 1000. Once engaged, the catheter 10 can be moved through the urethra 2600 by using the catheter mating device 1000 either to push and advance, or pull and retract, the catheter 10.

When in their second, expanded position, the tips 1174 (as measured when they are not restricted by a structure, such as the inner wall of mating chamber 16B or another structure), can have a maximum outer distance across them that is the same, or greater than, the diameter of mating chamber 16B (or other inner portion of catheter 10, such as lumen 14, because mating chamber 16B need not be used) in order for tips 1174 to create an interference fit against the inner wall of mating chamber 16B (or other structure). The tips 1174 can be comprised of any suitable material, such as a plastic, metal, or a thermoplastic elastomer.

In some embodiments, the tips 1174 at distal end 1170 form a tapered configuration such that they facilitate proper alignment of the tips 1774 and engagement chamber 16B so that tips 1774 can be received inside of chamber 16B (or other structure of catheter 10, such as lumen 14). Tips 1174 may have rounded end portions 1175 that assist in engaging proximal end 16.

Figure 16:
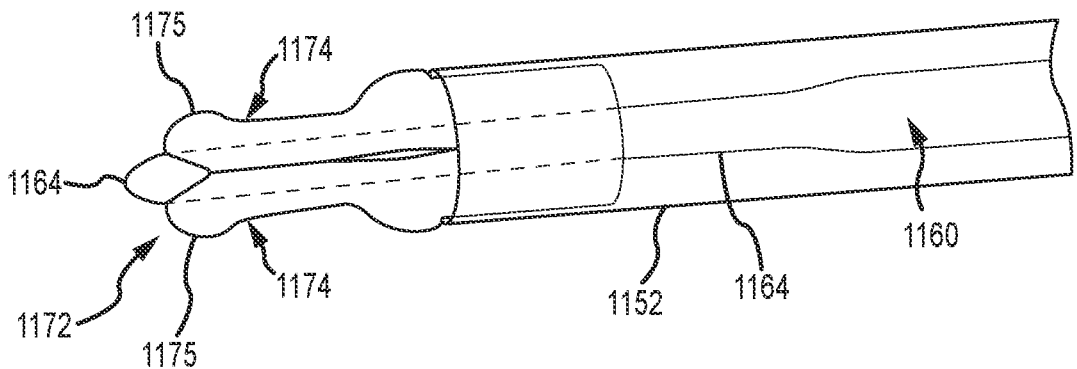
FIG. 16 is a side, perspective, close-up view of the distal end of the stem of the catheter mating device of FIG. 14.
Figure 16A:
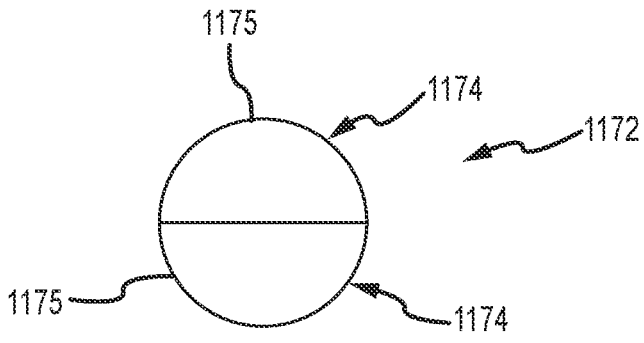
FIGS. 16A and 16B are front views of the distal end of the stem of the catheter mating device of FIG. 14.
Figure 16B:
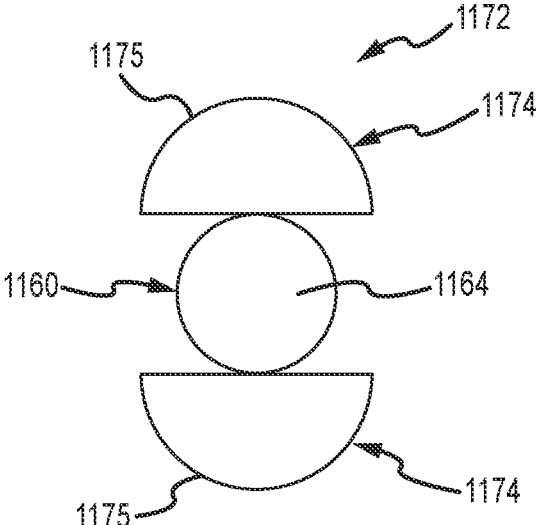
Figure 16C:
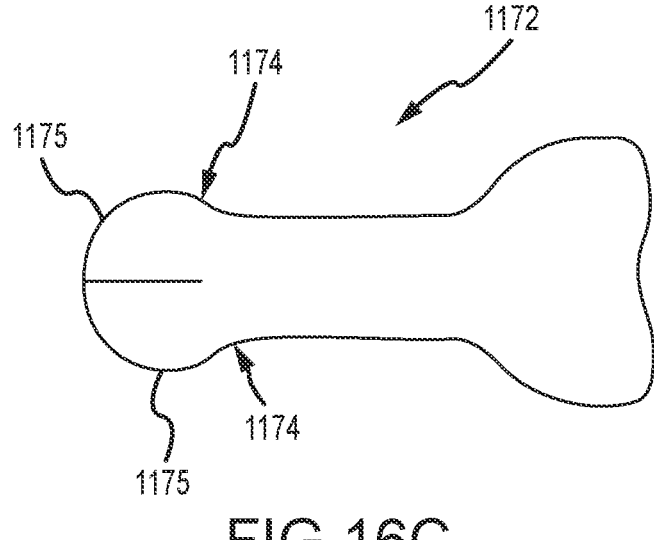
FIGS. 16C and 16D are partial, side views of the distal end of the stem of the catheter mating device of FIG. 14.
Figure 16D:
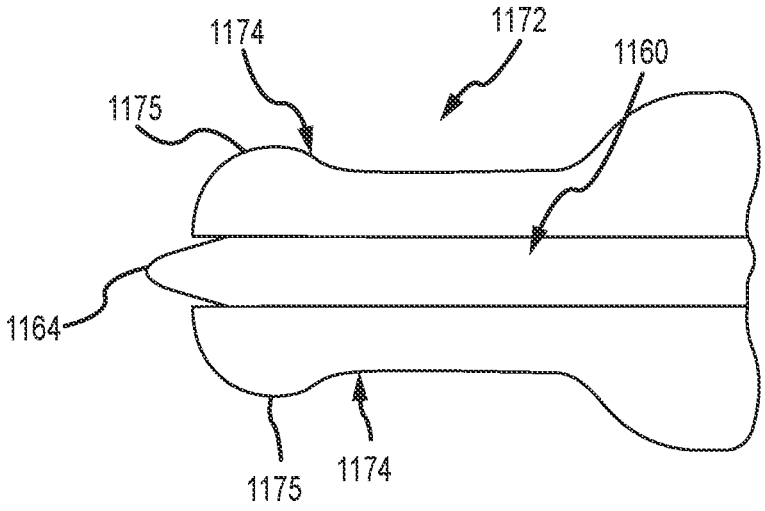
Figure 17:
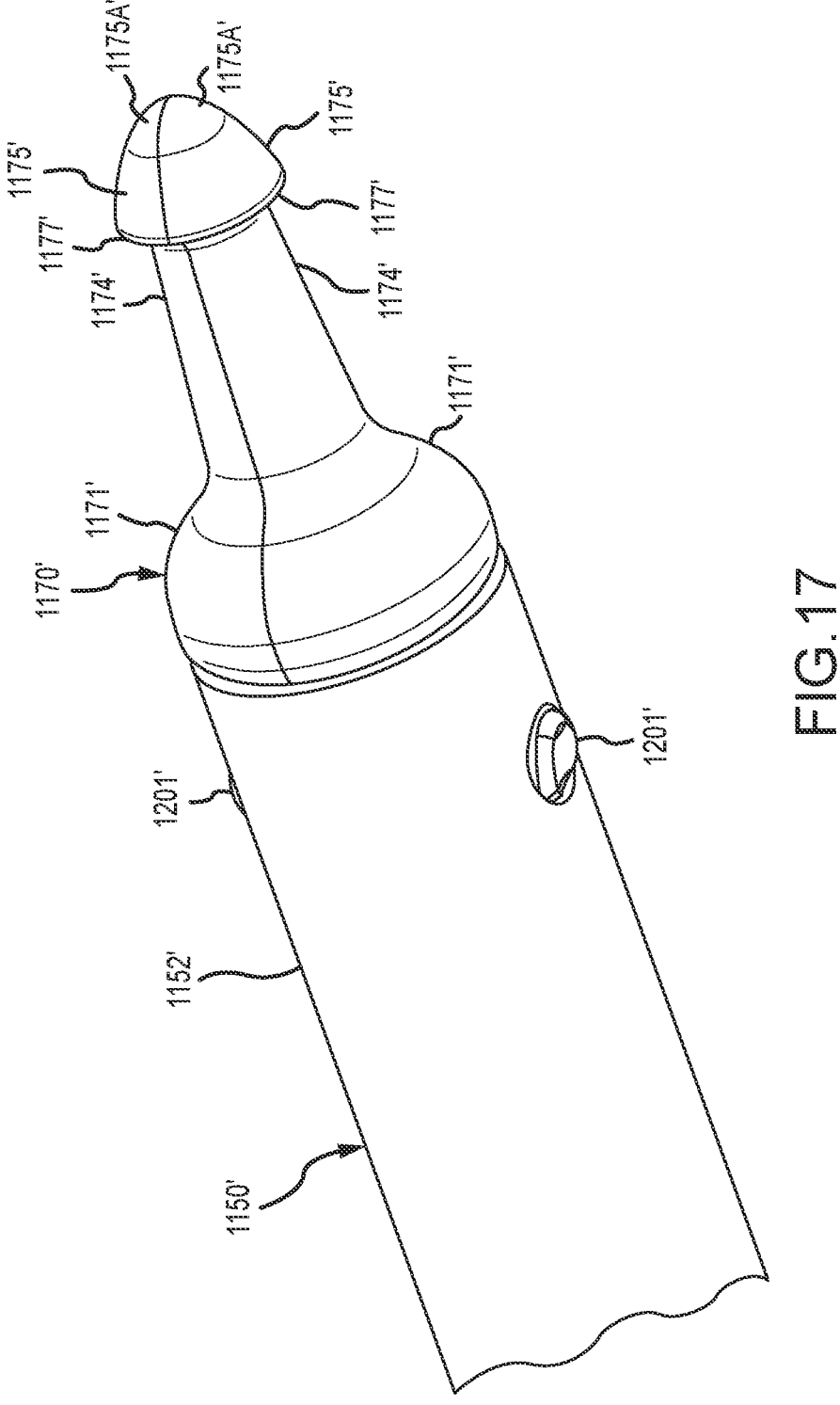
FIG. 17 is a partial, side perspective view of an alternate distal stem that may be used with a catheter mating device.
Figure 18:
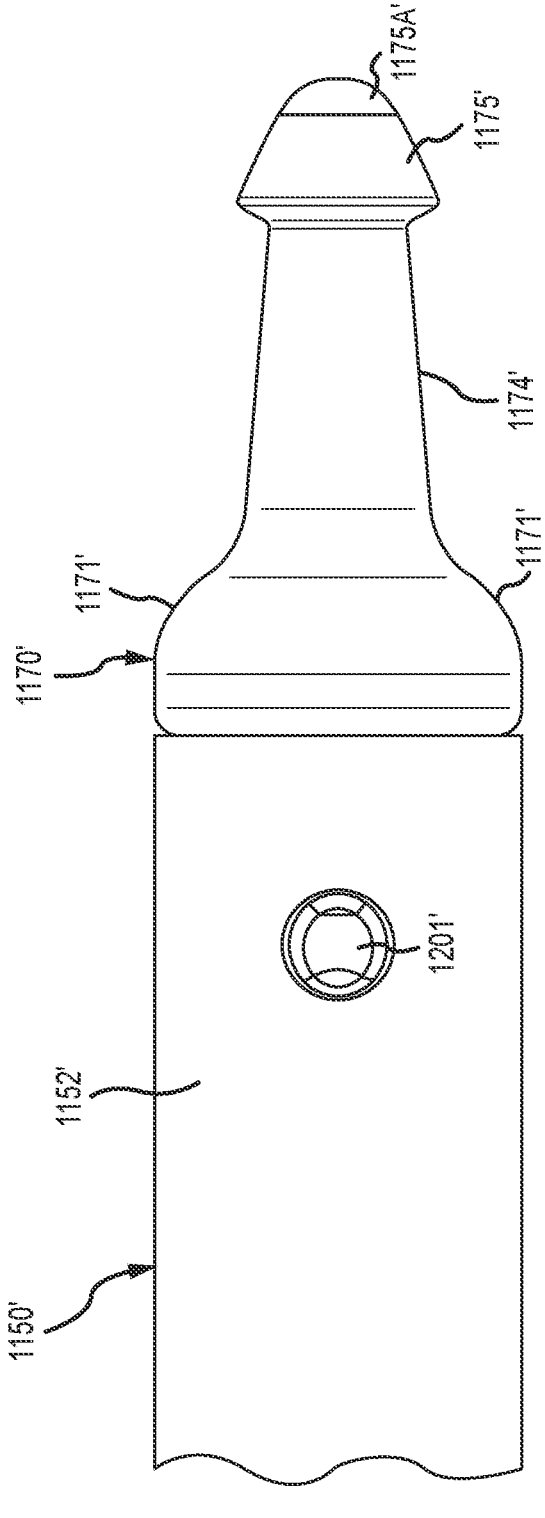
FIG. 18 is a partial, side view of the alternate distal stem of FIG. 17.
Figure 19:
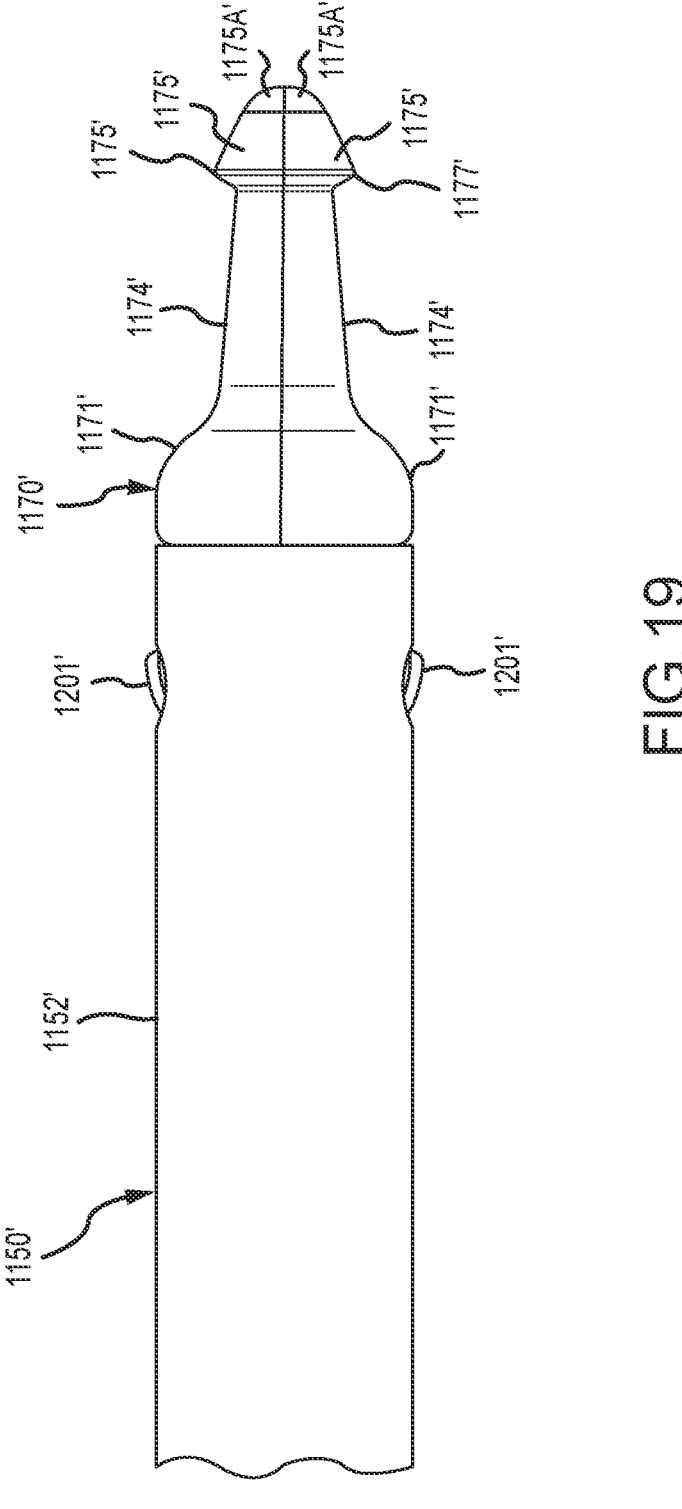
FIG. 19 is a partial, top view of the alternate distal stem of FIG. 17.
Figure 20:
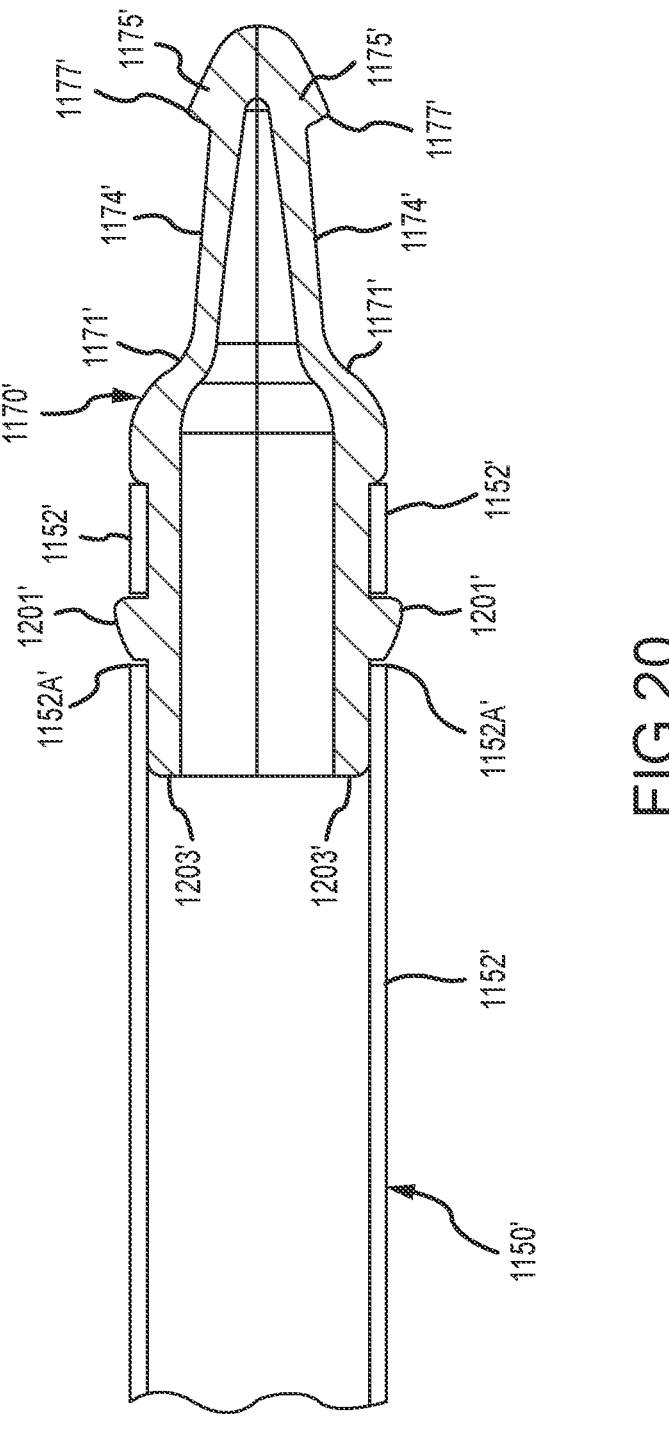
FIG. 20 is a partial, cross-sectional view of the alternate distal stem of FIG. 19.

The catheter mating device 1000 comprises a cylinder 1160 positioned inside of outer tube 1152. The cylinder 1160 is operated to move from a retracted position to an extended position. When cylinder 1160 is in its extended position (as shown in FIGS. 16, 16B, and 16D), the cylinder 1160 moves between the tips 1174 and pushes them open to their second, extended position. When cylinder 1160 is in its retracted position (as shown in FIGS. 16A, 16C, and 17-20 (showing an alternate embodiment)) the tips are in their first, retracted position. The cylinder 1160 may be comprised of any suitable material, such as ABS or PTFE, and preferably has a tapered distal end 1164.

A user may operate the catheter mating device 1000 by moving the control 1520 to its second position, which move the apparatus 1172 to its second, expanded position, and by moving the control 1520 to its first position, in which the apparatus 1172 either moves to, or is moved to its first, retracted position. In the embodiment shown, control 1520 is a slide switch directly or indirectly connected to cylinder 1160. When control 1520 is in its first position, the cylinder 1160 is in its first, retracted position. When control 1520 is moved to its second position, cylinder 1160 is moved to its second, extended position, wherein it moves between tips 1174 and pushes them open to their second, expanded position.

The stem 1150 in this embodiment has a length configured to enable a user to place catheter 10 in the urinary tract using the catheter mating device 1000. For example, in this embodiment stem 1150 may have a lengths (a) greater than the length of the penile urethra of a patient, (b) less than or equal to the length as measured from the membranous portion to the urethral orifice of a patient, and/or (c) less than the length of the penile urethra of a patient. In some embodiments, the stem 1150 is about 10 cm to 26 cm in length. Stem 1150 can include a fluid opening 1162 that is configured to allow fluid flow from the catheter 10 to pass through the lumen 1164 of stem 1150 and out of the proximal end 1152A of tube 1152, where the fluid can be collected or disposed, or pass through housing 1500 to be collected or disposed.

The tips of the tool and the cylinder may be designed in a configuration such that the maximum outer dimension of the tips in the expanded configuration is smaller than the stem. This may aid in preventing any unnecessary tissue damage to the penile urethra in the event that the user inserts or remove the tool with the tips in the expanded configuration without the catheter attached.

The catheter mating device 1000 may comprise an alternate stem 1150' that includes: (a) a tube 1152' having an outer surface (or external wall) 1154' and a lumen 1162, (b) an inner cylinder 1160 having a distal end 1160A and a proximal end 1160B connected to a control 1520, and (c) a distal end 1170' with apparatus 1172'. All components of stem 1150' are the same as for stem 1150 except as noted here. In all other respects, the structure and function of a catheter mating device 1000 is the same as previously described.

Turning now to FIGS. 17-20, an alternate distal stem 1150' of a catheter mating device 1000 is shown. Stem 1150' comprises an apparatus 1170' with tips 1174' that have a conical shape with a rounded end 1175' and lip, or ledge, 1177'. This configuration better assists tips 1174' in retaining end 16 of tube 12. Tips 1174' are configured to be positioned inside proximal end 16 (such as inside of engagement chamber 16B) when tips 1174' are in their first, retracted position. In that position tips 1174' have a first distance between them (which may be zero distance because tips 1174' may touch when in the first, retracted position) as best seen in FIGS. 17-20. Tips 1174' can be moved to their second, expanded position (not shown) in which they have a second distance between them that is larger than the first distance, as with tips 1174. In the second, expanded position, tips 1174' engage the inner wall of engagement chamber 16B, which connects catheter 10 to catheter mating device 1000. Once engaged, the catheter 10 can be moved through the urethra 2600, as shown best in FIG. 15, by using the catheter mating device 1000 either to push and advance, or pull and retract, the catheter 10.

Each tip 1174' has a outwardly curved section 1172', a recess 1171', a wall 1203', and a projection 1201'. Wall 1152' or stem 1150' includes openings 1152A'. Each wall 1203' is pressed into channel 1160 of stem 1150' until projection 1201' reaches an opening 1152' and extends therethrough. This mechanically retains a tip 1174' in position.

When in their second, expanded position, the tips 1174' (as measured when they are not restricted by a structure, such as the inner wall of mating chamber 16B or another structure), can have a maximum outer distance across them that is the same, or greater than, the diameter of mating chamber 16B (or other inner portion of catheter 10, such as lumen 14, because mating chamber 16B need not be used) in order for tips 1174' to create an interference fit against the inner wall of mating chamber 16B (or other structure). The tips 1174' can be comprised of any suitable material, such as a plastic, metal, or a thermoplastic elastomer.

In some embodiments, the tips 1174' at distal end 1170' form a tapered configuration such that they facilitate proper alignment of the tips 1774' and engagement chamber 16B so that tips 1174' can be received inside of chamber 16B (or other structure of catheter 10, such as lumen 14).

Housing

Figure 15:
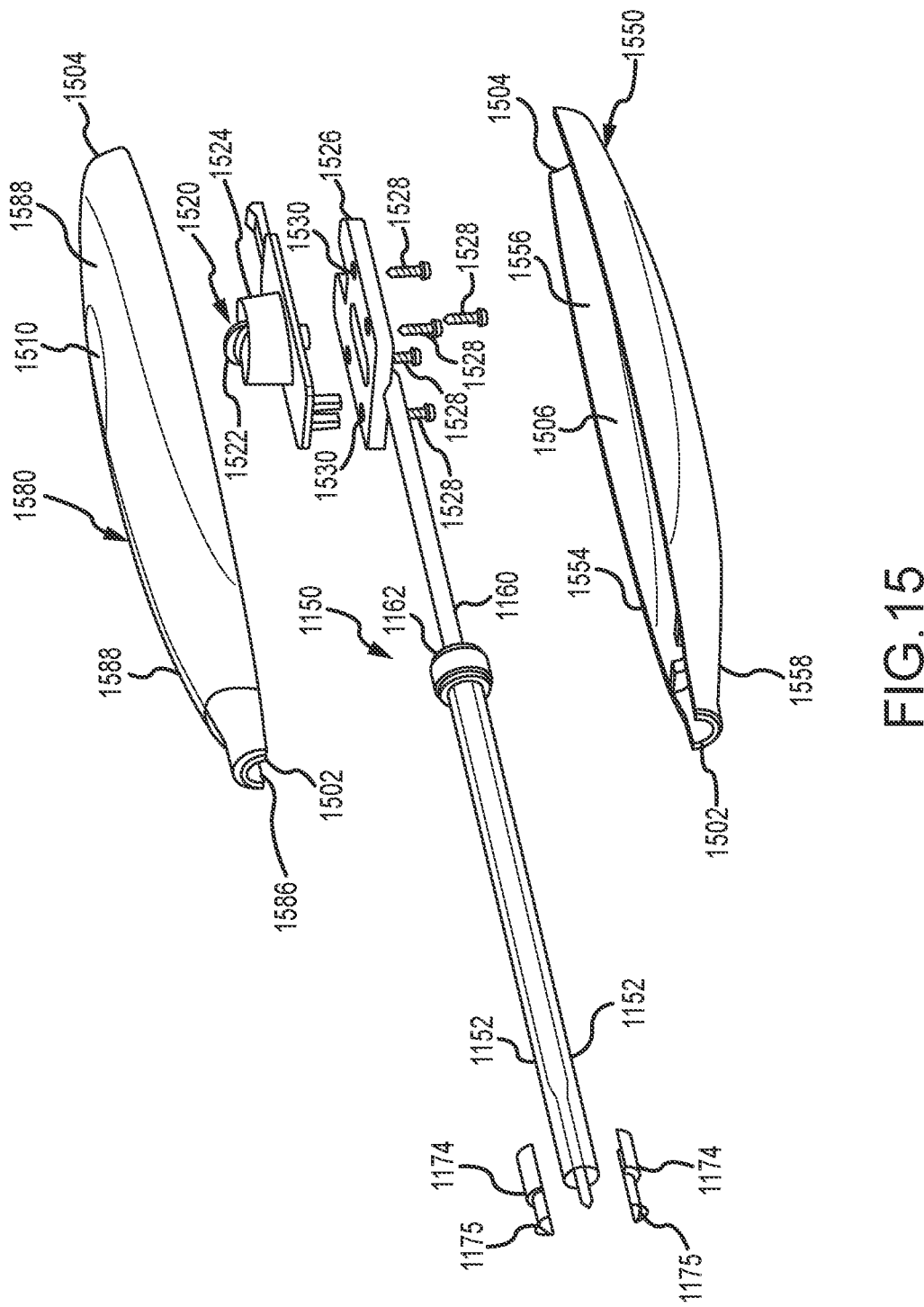
FIG. 15 is an exploded view of the catheter mating device of FIG. 14.

The catheter retention structure 1000 can have a handle (or housing) 1500 at its proximal end. Housing 1500 may house a portion of the stem 1150 and/or cylinder 1160, and includes a control 1520. The housing 1500 is comprised of any suitable material such as PVC or other plastic. Housing 1500 has body portion 1500A, which can be formed of two connected portions 1550 and 1580 as shown in FIG. 15. Body portion 1500A has a distal end 1502, a proximal end 1504, and a cavity 1506. An opening 1510, which communicates with cavity 1506, is in surface 1588. A control 1520 is positioned in cavity 1506 and extends through opening 1510 where it can be accessed by a user.

As shown, control 1520 is a slide switch that can be moved from a first (proximal) position to a second (distal position). Control 1520 has a ridge 1522 that can be pushed by a user's finger, a body portion 1524 that extends through opening 1510, and a base 1526 positioned in cavity 1506. Fasteners 1528 extend through apertures 1530 to retain control in housing 1500.

In the embodiment shown, cylinder 1160 is connected to control 1520. A user can move switch 1520 in a distal direction to push cylinder 1160 to its extended position, wherein the cylinder 1160 moves the apparatus to its second, expanded position. A user can move switch 1520 in a proximal direction, wherein the cylinder 1160 moves to its retracted position away from the apparatus 1172 and the apparatus moves to its first, retracted position. Although a manual slide switch is described herein, control 1520 could be any structure that can operate to directly or indirectly move the apparatus to its second, expanded position.

The proximal end 1152A of tube 1152 is retained inside of cavity 1506. If fluid enters lumen (or passageway) 1164 it exits the proximal end 1152A, and can flow through housing 1500, where it exits opening 1504A at proximal end 1504. This allows for relatively easy collection or disposal of fluid from the body in which catheter 10 is positioned. In one embodiment, the stem 1150 has a length of about 10 cm to 26 cm.

Materials

The catheter 10 and the stem 1170 of catheter mating device 1000 are, respectively, constructed in a shape and of a material that is conducive for their intended use. For example, the catheter 10 and stem 1170 may be constructed of any material or materials suitable for catheters used in the body (such as PVC, latex, silicone, polyurethane or any suitable blend of these materials).

Wireless Controller

Figure 13:
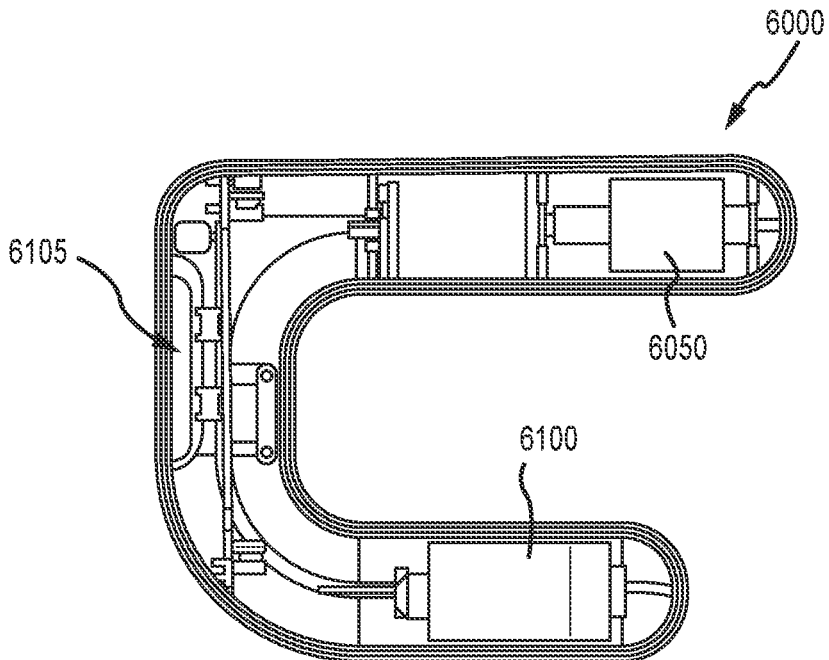
FIG. 13 shows a side, open view an exemplary embodiment of a wireless controller for operating a valve.
Figure 14:
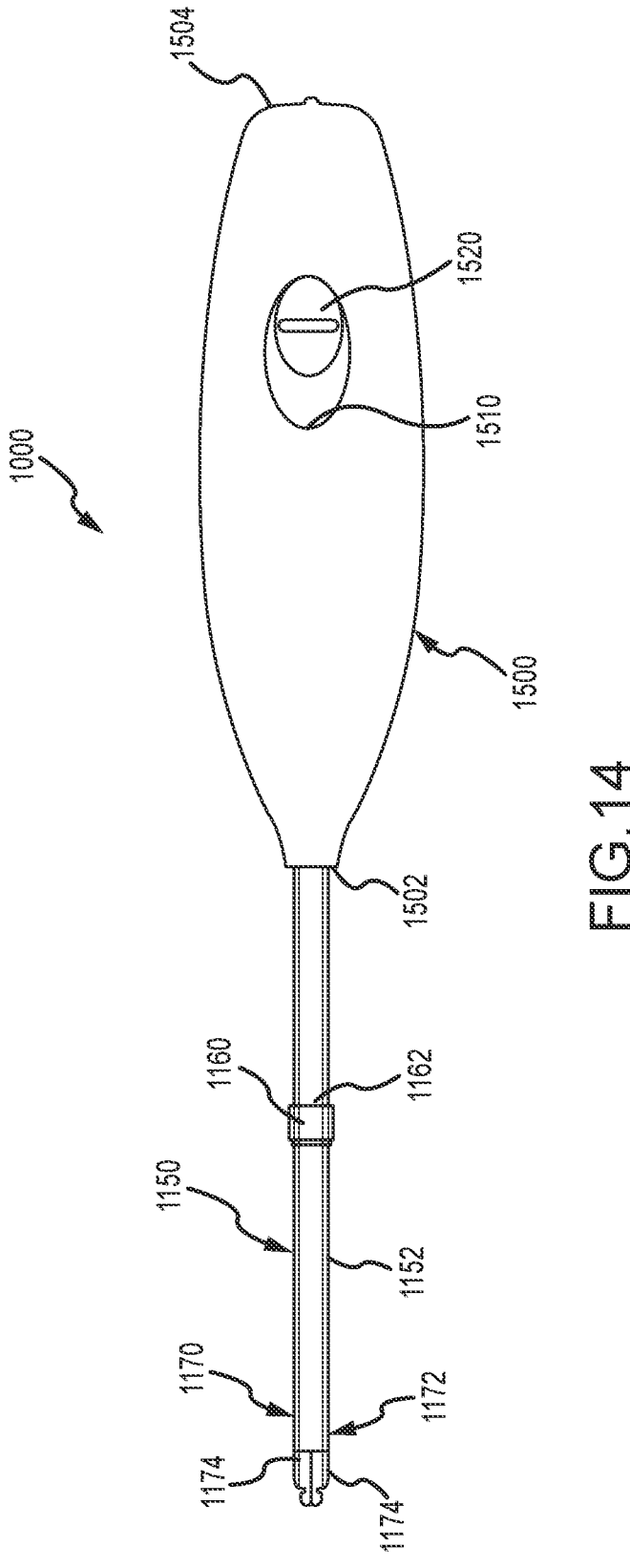
FIG. 14 shows a top view of an exemplary catheter mating device.

Urine in the bladder (or fluid from another area in the body) can be voided when the user utilizes an external wireless controller 6000 (shown in FIG. 13) to operate the valve 100 and allow urine to travel through the lumen 14, past proximal end 16, and out of catheter 10. The wireless controller 6000 can comprise an wireless controller magnet 6050, a power source 6100, and an electronic circuitry 6150. One or more inputs can comprise a first input to open the valve 100 and a second input to close the valve 100. The wireless controller 6000 comprises two or more input modes, such as a close mode, an open mode, and an off mode. The valve 100 is closed (or off) when the wireless controller 6000 is in its close mode, and is open (or in operation) when the wireless controller is in its open mode. The valve 100 can remain closed or remain opened when the wireless controller 6000 is in its off mode. In some embodiments, the circuitry 6150 can comprise software configured to automate the process of controlling fluid flow from bladder. A user can place the wireless controller 6000 near the valve 100, e.g., on the skin of the patient between the scrotum and the shaft of the penis. The user may operate the input to operate the magnet 6050.

Sensors and Data Collection

The catheter 10 can include one or more sensors configured to transmit data from the patient's body. As used herein, any sensor used with a catheter according to the invention is referenced by numeral. Thus, one or more sensors refers to a single sensor and a plurality of sensors. The data can comprise one or more of: fluid pressure of urine in the bladder and/or urethra, volume of fluid in the bladder, temperature of fluid in the bladder and/or urethra, acidity of fluid in the bladder and/or urethra, bacteria type and quantity of fluid in the bladder and/or urethra, chemical composition of fluid of fluid in the bladder and/or urethra, fluid flow during emptying of the bladder when valve 100 is open, or actuated. One or more sensors as described in this disclosure are of a type known to those skilled in the relevant art, although the claims are not limited to presently-known sensors. One or more sensors on or inside of catheter 10D would have basically consistent sensor location and extended sensors measurements within the body to better monitor patient conditions, without having sensors taken out of the body.

In one embodiment, the one or more sensors can determine the pressure of urine within the bladder and send a signal to a processor that sends the information to a computing device, or the one or more sensors could send data directly to the computing device. The computing device, which can be any device, such as a PC or other computer, cell phone, dedicated catheter device, the wireless controller, or the catheter mating device, can have software that determines whether and when fluid (such as urine) needs to be drained from the bladder. The computing device can notify the user in any manner to drain urine from his/her bladder. In some embodiments, the one or more sensors can be used to determine when urine has been sufficiently drained from the bladder, such as by determining that the pressure level within the bladder has dropped below a certain level. This information can be used to close the valve 100 and halt the flow of urine from leaving the bladder. In some embodiments, the one or more sensors can include acoustics to determine the volume of urine in the bladder. Different types of sensors can be placed in or on the catheter 10 to determine metrics related to the health of areas of the body, such as bladder health.

The data collected by the one or more sensors can be stored, analyzed, and/or transmitted via software resident on a device outside of the body in which one or more sensors is positioned. The software may utilize machine-learning algorithms to predict and interpret the measurements.

Some Non-Limiting Examples of this Disclosure

Following are Some Non-Limiting Examples of this Disclosure

Example 1: A urinary catheter comprising:
(a) a tube having (i) a wall with an outer surface, the outer surface having a first cross-sectional area, (ii) a lumen, (iii) a distal end with one or more openings in communication with the lumen, and (iv) a proximal end with an opening in communication with the lumen;

(b) a valve that is operated to be in (i) a closed configuration, wherein fluid does not flow out of the proximal end, or (ii) an open configuration in which fluid does flow out of the proximal end; and (c) a retainer between the distal end and the proximal end, the retainer being attached to the tube and including an outwardly-extending flap, wherein the retainer has a first, compressed position in which it is pressed against and/or around the outer surface of the tube and is configured to fit through the penile urethra, and a second, extended position in which it extends outward from the tube by a distance of one to four times the outer diameter of the tube and is configured to not fit through the penile urethra.

Example 2: The urinary catheter of example 1, wherein the outwardly-extending flap has an outermost edge that comprises a bulb.

Example 3: The urinary catheter of example 1 or example 2, wherein the retainer flap has a center portion with a thickness that is the same as or greater than a thickness of the tube wall, Example 4: The urinary catheter of example 3, wherein the thickness is 0.75 mm to 1.0 mm.

Example 5: The urinary catheter of any one of examples 1-4, wherein the bulb has a diameter that is greater than the thickness.

Example 6: The urinary catheter of any one of examples 1-5, wherein the retainer has a hardness of an amount from: 1 to 70 Shore A, 5-15 Shore A, 10-20 Shore A, 5-15 Shore A, or 10-15 Shore A.

Example 7: The urinary catheter of any one of examples 1-6, wherein the retainer is comprised of silicone rubber.

Example 8: The urinary catheter of any of examples 1-7, wherein the retainer can be moved from its first, extended position to its second, compressed position when subjected to a compressive force of an amount from 0.5-2.5 lbs.

Example 9: The urinary catheter of any of examples 1-8, wherein the retainer has an axial length measured where it is attached to the tube of 25 mm-35 mm.

Example 10: The urinary catheter of any one of examples 3-9, wherein the retainer portion further comprises a first, rounded corner between a first side of the center portion and the outermost edge and a second, rounded corner between a second side of the center portion and the outermost edge.

Example 11: The urinary catheter of any of examples 1-10 that further includes one or more sensors on or in the catheter and that is configured such that the one or more sensors are positioned in a bladder when the urinary catheter is positioned in a lower urinary tract of a human.

Example 12: The urinary catheter of any of examples 1-11, that further includes a bladder retention structure juxtaposed the distal end of the tube.

Example 13: The urinary catheter of example 12, wherein the bladder retention structure comprises an attachment portion attached to the tube, wherein the attachment portion has a distal side and a proximal side, a first leg connected to the distal side of the attachment portion, a second leg connected to the proximal side of the attachment portion, a center portion connected to the first leg and to the second leg opposite the attachment portion, wherein the bladder retention structure has a first, compressed position in which at least part of the center portion presses against the attachment portion, and a second, extended portion in which the center portion extends outward from the attachment portion by a distance of 2-5 times the width of the tube.

Example 14: The urinary catheter of example 12 or example 13, wherein the first leg of the bladder retention structure is curved backwards from where it is connected to the attachment structure.

Example 15: The urinary catheter of any one of examples 12-14, wherein the second leg of the bladder retention structure is curved backwards from where it is connected to the attachment structure.

Example 16: The urinary catheter of any one of examples 12-15, wherein the center portion of the bladder retention structure has an intermediate section that is straight.

Example 17: The urinary catheter of any of examples 12-16, wherein the bladder retention structure has a thickness that is from equal to, to four times greater than, a thickness of the tube wall.

Example 18: The urinary catheter of any of examples 1-17 that further comprises a bladder retention structure on the distal end, wherein the bladder retention structure has a second, compressed position in which it is positioned against and/or around the outer surface of the tube, and a first, extended position in which it extends outward from the outer wall of the tube.

Example 19: The urinary catheter of any of examples 1-18, wherein the distal tip is bullet shaped and has a hardness that is greater than the harness of the tube wall.

Example 20: The urinary catheter of any of any of examples 1-19, wherein the distal tip has a conical first portion that tapers from a diameter equal to a diameter of the tube wall to a rounded end portion.

Example 21: The urinary catheter of any of examples 1-20, wherein the wall of the catheter has a hardness of between 30 Shore A and 55 Shore D.

Example 22: The urinary catheter of any of examples 1-21, wherein the retainer is comprised of silicone rubber.

Example 23: The urinary catheter of any of examples 1-22, wherein the retainer is positioned between the valve and the distal end.

Example 24: The urinary catheter of any of examples 1-23 that is configured to be completely retained inside of a urinary tract of a male human.

Example 25: The urinary catheter of any of examples 1-24, wherein the retainer extends outward from the outer surface of the tube wall.

Example 26: The urinary catheter of any of examples 1-25, wherein the retainer is configured to be compressed to extend outwards a maximum distance of 0.3 mm to 8.0 mm from the outer surface of the tube wall when moved through a penile urethra.

Example 27: The urinary catheter of any of examples 1-26, wherein at least part of the retainer is configured to be positioned within the bulbar urethra of the patient when the catheter is positioned inside a urinary tract of a human male.

Example 28: The urinary catheter of any of examples 1-27, wherein the retainer is positioned on the tube.

Example 29: The urinary catheter of example 28, wherein the retainer includes a passage therethrough and part of the tube is positioned in the passage.

Example 30: The urinary catheter of any one of examples 1-29, wherein the retainer has (a) a distal section that has (a) a smaller cross-sectional area than the maximum cross-sectional area, and (b) a proximal section that has a smaller cross-sectional area than the maximum cross-sectional area.

Example 31: The urinary catheter of any of examples 1-30, wherein the valve is a magnetic valve.

Example 32: The urinary catheter of any of examples 1-31, wherein the valve is positioned in the lumen.

Example 33: The urinary catheter of any of examples 1-32 that further includes an engagement chamber at the proximal end, wherein the engagement chamber is about 10 Shore A to 55 Shore D harder than the wall.

Example 34: The urinary catheter of any of examples 1-32 that further includes an engagement chamber that has a diameter that is the same as a diameter of the lumen.

Example 35: The urinary catheter of any of examples 1-34 that further includes a catheter mating device comprising a housing connected to a proximal end of a stem of the catheter mating device.

Example 36: The urinary catheter of example 35, wherein the proximal end of the stem is positioned inside of the housing.

Example 37: The urinary catheter of any of examples 35-36, wherein the stem has an internal passageway configured to the transport bodily fluid.

Example 38: The urinary catheter of any one of examples 12-37 that includes a plurality of bladder retention structures.

Example 39: The urinary catheter of example 38, wherein at least one of the plurality of retention structures has a different size or shape than the other of the plurality of retention structures.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result. No language in the specification should be construed as indicating that any non-claimed limitation is included in a claim. The terms "a" and "an" expressly used in the context of describing the invention (especially in the context of the following claims) are to be construed to cover both the singular and the plural, unless otherwise indicated herein or clearly contradicted by context.

What is claimed is:

1. A urinary catheter comprising:

(a) a tube having (i) a wall with an outer surface, the outer surface having a first cross-sectional area, (ii) a lumen, (iii) a distal end with one or more openings in communication with the lumen, and (iv) a proximal end with an opening in communication with the lumen;

(b) a valve that is operated to be in (i) a closed configuration, wherein fluid does not flow out of the proximal end, or (ii) an open configuration in which fluid does flow out of the proximal end; and (c) a retainer between the distal end and the proximal end, the retainer being attached to the tube and including an outwardly-extending flap, wherein the retainer has a first, compressed position in which it is pressed against and/or around the outer surface of the tube and is configured to fit through the penile urethra, and a second, extended position in which it extends outward from the tube by a distance of one to four times the outer diameter of the tube and is configured to not fit through the penile urethra, wherein the outwardly-extending flap comprises a center portion extending from the tube, wherein the center portion comprises an axial length between about 25 mm and about 35 mm in a first direction defined from the distal end to the proximal end, a second length in a second direction orthogonal to the first direction and extending from an outer wall of the tube, and a center portion thickness in a third direction orthogonal to the first direction and the second direction, and wherein the second length is about 40% to about 800% of a diameter of the tube, wherein the outwardly-extending flap further comprises an outermost edge extending from the center portion in the second direction, wherein the outermost edge comprises a bulb with a bulb thickness in the third direction greater than the center portion thickness.

2. The urinary catheter of claim 1, wherein the center portion thickness is the same as or greater than a thickness of the tube wall.

3. The urinary catheter of claim 2, wherein the center portion thickness is 0.75 mm to 1.0 mm.

4. The urinary catheter of claim 2, wherein the retainer further comprises a first, rounded corner between a first side of the center portion and an outermost edge and a second, rounded corner between a second side of the center portion and the outermost edge.

5. The urinary catheter of claim 1, wherein the bulb thickness is 10% to 100% greater than the center portion thickness.

6. The urinary catheter of claim 1, wherein the retainer has a hardness of an amount from: 1 to 70 Shore A, 5-15 Shore A, 10-20 Shore A, 5-15 Shore A, or 10-15 Shore A.

7. The urinary catheter of claim 1, wherein the retainer is comprised of silicone rubber.

8. The urinary catheter of claim 1, wherein the retainer can be moved from its first, extended position to its second, compressed position when subjected to a compressive force of an amount from 0.5-2.5 lbs.

9. The urinary catheter of claim 1, wherein the second length and the diameter of the tube is about 15 mm to about 25 mm, and wherein the center portion thickness is between about 0.75 mm and about 1.0 mm.

10. The urinary catheter of claim 9, wherein the outwardly-extending flap further comprises an outermost edge extending from the center portion in the second direction, wherein the outermost edge comprises a bulb with a bulb thickness in the third direction 10% to 100% greater than the center portion thickness.

11. The urinary catheter of claim 10, wherein the bladder retention structure has a thickness that is from equal to, to four times greater than, a thickness of the tube wall.

12. The urinary catheter of claim 1 that further includes one or more sensors on or in the catheter and that is configured such that the one or more sensors are positioned in a bladder when the urinary catheter is positioned in a lower urinary tract of a human.

13. The urinary catheter of claim 1, further comprising a bladder retention structure, wherein the bladder retention structure comprises an attachment portion attached to the tube, wherein the attachment portion has a distal side and a proximal side, a first leg connected to the distal side of the attachment portion, a second leg connected to the proximal side of the attachment portion, a center portion connected to the first leg and to the second leg opposite the attachment portion, wherein the bladder retention structure is configured to have a second, extended position in which the center portion extends outward from the attachment portion by a distance of 2-5 times the width of the tube.

14. The urinary catheter of claim 13, wherein the first leg of the bladder retention structure is curved backwards from where it is connected to the attachment structure.

15. The urinary catheter of claim 13, wherein the second leg of the bladder retention structure is curved backwards from where it is connected to the attachment structure.

16. The urinary catheter of claim 13, wherein the center portion of the bladder retention structure has an intermediate section that is straight.

17. The urinary catheter of claim 1 that further comprises a bladder retention structure on the distal end, wherein the bladder retention structure has a second, compressed position in which it is positioned against and/or around the outer surface of the tube, and a first, extended position in which it extends outward from the outer wall of the tube.

18. The urinary catheter of claim 1, wherein the distal tip is bullet shaped and has a hardness that is greater than the harness of the tube wall.

19. The urinary catheter of any of claim 1, wherein the distal tip has a conical first portion that tapers from a diameter equal to a diameter of the tube wall to a rounded end portion.

*    *    *    *    *